（12）United States Patent
Kallmyer et al.

(10) Patent No.: US 10,322,288 B2
(45) Date of Patent: Jun. 18, 2019

(54) HEAT MANAGEMENT FOR RECHARGE COILS FOR IMPLANTABLE MEDICAL DEVICES

(75) Inventors: Todd A. Kallmyer, Tempe, AZ (US); John E. Kast, Hugo, MN (US); David P. Olson, Minnetrista, MN (US); Randy S. Roles, Elk River, MN (US); Venkat R. Gaddam, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1649 days.

(21) Appl. No.: 13/284,804

(22) Filed: Oct. 28, 2011

(65) Prior Publication Data
US 2013/0106347 A1    May 2, 2013

(51) Int. Cl.
| | |
|---|---|
| *A61N 1/375* | (2006.01) |
| *A61N 1/378* | (2006.01) |
| *H02J 50/10* | (2016.01) |
| *H02J 50/90* | (2016.01) |
| *A61N 1/08* | (2006.01) |
| *H02J 7/02* | (2016.01) |

(Continued)

(52) U.S. Cl.
CPC .............. *A61N 1/3787* (2013.01); *A61N 1/08* (2013.01); *A61N 1/36142* (2013.01); *A61N 1/375* (2013.01); *H02J 5/005* (2013.01); *H02J 7/025* (2013.01); *H02J 17/00* (2013.01); *H02J 50/10* (2016.02); *H02J 50/90* (2016.02); *A61N 1/37211* (2013.01)

(58) Field of Classification Search
CPC .... A61N 1/3787; A61N 1/08; A61N 1/13142; A61N 1/375; A61N 1/37211; H02J 7/025; H02J 17/00; H02J 5/005

USPC ............................... 62/56, 259.3, 530
See application file for complete search history.

(56) References Cited

U.S. PATENT DOCUMENTS

| 4,226,364 A | 10/1980 | Utesch |
| 4,819,662 A * | 4/1989 | Heil et al. ..................... 607/116 |

(Continued)

FOREIGN PATENT DOCUMENTS

| WO | 2005037365 A1 | 4/2005 |
| WO | 2009029977 A1 | 3/2009 |

OTHER PUBLICATIONS

Response to Office Action dated Oct. 16, 2013, from U.S. Appl. No. 13/284,680, filed Jan. 16, 2014, 14 pages.

(Continued)

*Primary Examiner* — David J Teitelbaum
(74) *Attorney, Agent, or Firm* — Shumaker & Sieffert, P.A.

(57) ABSTRACT

Devices, systems, and techniques for managing heat generated in coils for wireless energy transmission are disclosed. Inductive coupling between two coils may be used to recharge the power source of an implantable medical device. A phase change material may be thermally coupled to a flexible coil to absorb heat generated during the inductive coupling and reduce temperature increases of the flexible coil. The flexible coil may be configured to at least one of transmit energy to or receive energy from a second coil, and the phase change material may be configured to deform with the flexible coil and absorb heat from the flexible coil. The phase change material may be contained within thermally conductive tubes or channels configured in shapes that promote flexibility of the flexible coil.

35 Claims, 10 Drawing Sheets

(51) Int. Cl.

| | |
|---|---|
| *A61N 1/36* | (2006.01) |
| *H02J 5/00* | (2016.01) |
| *H02J 17/00* | (2006.01) |
| *A61N 1/372* | (2006.01) |

(56) References Cited

U.S. PATENT DOCUMENTS

| | | | |
|---|---|---|---|
| 5,669,584 A * | 9/1997 | Hickey | 244/171.7 |
| 5,755,110 A * | 5/1998 | Silvas | 62/259.3 |
| 5,884,006 A | 3/1999 | Frohlich et al. | |
| 5,984,953 A * | 11/1999 | Sabin et al. | 607/114 |
| 6,108,489 A | 8/2000 | Frohlich et al. | |
| 6,277,143 B1 | 8/2001 | Klatz et al. | |
| 6,308,518 B1 * | 10/2001 | Hunter | F25B 21/02 62/3.3 |
| 6,349,234 B2 | 2/2002 | Pauly et al. | |
| 6,384,703 B1 | 5/2002 | Ramos et al. | |
| 6,419,621 B1 * | 7/2002 | Sioshansi et al. | 600/3 |
| 6,545,253 B2 | 4/2003 | Lin et al. | |
| 6,699,266 B2 | 3/2004 | Lachenbruch et al. | |
| 6,755,852 B2 | 6/2004 | Lachenbruch et al. | |
| 6,852,956 B2 | 2/2005 | Rock et al. | |
| 6,895,281 B1 * | 5/2005 | Amundson et al. | 607/60 |
| 6,927,316 B1 * | 8/2005 | Faries et al. | 602/43 |
| 6,978,185 B2 * | 12/2005 | Osypka | 607/122 |
| 7,035,532 B2 * | 4/2006 | Kudo | F24H 7/0408 165/10 |
| 7,225,032 B2 | 5/2007 | Schmeling et al. | |
| 7,232,421 B1 * | 6/2007 | Gambale et al. | 604/57 |
| 7,286,880 B2 | 10/2007 | Olson et al. | |
| 7,286,881 B2 | 10/2007 | Schommer et al. | |
| 7,441,558 B2 | 10/2008 | Leifer et al. | |
| 7,486,048 B2 * | 2/2009 | Tsukamoto et al. | 320/112 |
| 7,505,816 B2 | 3/2009 | Schmeling et al. | |
| 7,512,443 B2 | 3/2009 | Phillips et al. | |
| 7,515,967 B2 | 4/2009 | Phillips et al. | |
| 7,744,640 B1 * | 6/2010 | Faries et al. | 607/109 |
| 7,774,069 B2 | 8/2010 | Olson et al. | |
| 8,209,024 B2 * | 6/2012 | Greenbaum et al. | 607/53 |
| 8,301,110 B2 | 10/2012 | Roberts | |
| 8,326,426 B2 | 12/2012 | Thornton et al. | |
| 8,498,716 B2 | 7/2013 | Chen | |
| 8,545,384 B2 | 10/2013 | Forsell | |
| 8,887,619 B2 | 11/2014 | Kallmyer et al. | |
| 2002/0151770 A1 | 10/2002 | Noll | |
| 2003/0085684 A1 * | 5/2003 | Tsukamoto et al. | 320/108 |
| 2003/0109910 A1 * | 6/2003 | Lachenbruch et al. | 607/108 |
| 2004/0106963 A1 * | 6/2004 | Tsukamoto et al. | 607/33 |
| 2005/0021100 A1 | 1/2005 | Tsukamoto et al. | |
| 2006/0156756 A1 | 7/2006 | Becke | |
| 2006/0191344 A1 * | 8/2006 | Hashimoto | A61B 8/00 73/632 |
| 2006/0247737 A1 | 11/2006 | Olson et al. | |
| 2006/0247738 A1 | 11/2006 | Schmeling et al. | |
| 2007/0096686 A1 | 5/2007 | Jimenez et al. | |
| 2007/0167997 A1 | 7/2007 | Forsberg | |
| 2008/0087270 A1 * | 4/2008 | Shaikh et al. | 126/263.01 |
| 2008/0197126 A1 * | 8/2008 | Bourke et al. | 219/634 |
| 2008/0221555 A1 * | 9/2008 | Sheppard | A61B 1/041 604/890.1 |
| 2009/0005770 A1 | 1/2009 | Gerber et al. | |
| 2009/0112291 A1 | 4/2009 | Wahlstrand et al. | |
| 2009/0157148 A1 | 6/2009 | Phillips | |
| 2010/0171368 A1 * | 7/2010 | Schatz | H01Q 1/248 307/104 |
| 2010/0174201 A1 * | 7/2010 | Bodecker et al. | 600/488 |
| 2010/0230653 A1 * | 9/2010 | Chen | 257/4 |
| 2010/0241194 A1 * | 9/2010 | Kast et al. | 607/61 |
| 2010/0256708 A1 * | 10/2010 | Thornton et al. | 607/61 |
| 2010/0268305 A1 * | 10/2010 | Olson et al. | 607/61 |
| 2010/0274308 A1 * | 10/2010 | Scott | 607/9 |
| 2011/0022125 A1 | 1/2011 | Olson | |
| 2011/0087192 A1 * | 4/2011 | Uhland | A61K 9/0036 604/514 |
| 2011/0100495 A1 * | 5/2011 | Welle | B01L 3/502738 137/827 |
| 2011/0106213 A1 | 5/2011 | Davis | |
| 2011/0110048 A1 * | 5/2011 | Lima | H05K 7/20418 361/720 |
| 2011/0118661 A1 * | 5/2011 | Pless et al. | 604/66 |
| 2011/0120673 A1 | 5/2011 | Xiang | |
| 2011/0172744 A1 * | 7/2011 | Davis | A61M 5/14276 607/62 |
| 2011/0175568 A1 * | 7/2011 | Leijssen et al. | 320/108 |
| 2011/0194114 A1 * | 8/2011 | Yeo | B01L 3/5027 356/435 |
| 2013/0106347 A1 | 5/2013 | Kallmyer et al. | |

OTHER PUBLICATIONS

Office Action from U.S. Appl. No. 14/542,032, dated Jan. 6, 2016, 17 pp.

International Search Report and Written Opinion of PCT/US2012/060386, dated Jan. 21, 2013, 12 pp.

Notice of Allowance from U.S. Appl. No. 13/284,680, dated Jul. 16, 2014, 7 pp.

Office Action from U.S. Appl. No. 13/284,680, dated Oct. 16, 2013, 10 pp.

U.S. Appl. No. 13/284,680, filed Oct. 28, 2011, "Removable Heat Management for Recharge Coils,".

Final Office Action from U.S. Appl. No. 13/284,680, dated Mar. 12, 2014, 13 pp.

Response to Office Action dated Mar. 12, 2014, from U.S. Appl. No. 13/284,680, filed May 12, 2014, 10 pp.

Notice of Allowance from U.S. Appl. No. 14/542,032, dated May 31, 2016, 7 pp.

Notice of Allowance from U.S. Appl. No. 14/542,032, dated Sep. 15, 2016, 7 pp.

* cited by examiner

HEAT MANAGEMENT FOR RECHARGE COILS FOR IMPLANTABLE MEDICAL DEVICES

TECHNICAL FIELD

The disclosure relates to wireless power transfer for implantable medical devices and, more particularly, to heat management in power transfer coils.

BACKGROUND

Implantable medical devices may be used to monitor a patient condition and/or deliver therapy to the patient. In long term or chronic uses, implantable medical devices may include a rechargeable power source (e.g., one or more capacitors or batteries) that extends the operational life of the medical device to weeks, months, or even years over a non-rechargeable device.

When the energy stored in the rechargeable power source has been depleted, the patient may use an external charging device to recharge the power source. Since the rechargeable power source is implanted in the patient and the charging device is external of the patient, this charging process may be referred to as transcutaneous charging. In some examples, transcutaneous charging may be performed via inductive coupling between a primary coil in the charging device and a secondary coil in the implantable medical device.

An electrical current applied to the primary coil generates a magnetic field, and when the primary coil is aligned to the secondary coil, the magnetic field induces an electrical current in the secondary coil within the patient. A charging circuit within the implantable medical device then applies current from the secondary coil to charge the rechargeable power source within the implantable medical device. With transcutaneous transfer via inductive coils, the external charging device does not need to physically connect with the rechargeable power source for charging to occur.

SUMMARY

In general, the disclosure is directed to devices, systems, and techniques for managing heat generated in coils for wireless energy transmission to implantable medical devices. Inductive coupling between two coils may be used to recharge the power source of an implantable medical device. A primary coil remains external to the patient and a secondary coil may be implanted with the implantable medical device. A phase change material may be disposed in thermal communication with a flexible coil, e.g., the primary and/or secondary coil, to absorb heat generated during the inductive coupling and reduce temperature increases of the flexible coil. The phase change material may also be shaped and/or positioned to deform with the flexible coil. In some examples, the phase change material may be contained within thermally conductive tubes or channels configured in shapes that promote flexibility of the flexible coil.

In one aspect, the disclosure is directed to a device that includes a flexible coil configured to at least one of transmit energy to or receive energy from a second coil and a phase change material configured to deform with the flexible coil, wherein the phase change material is configured to absorb heat from the flexible coil.

In another aspect, the disclosure is directed to a device that includes a flexible coil configured to at least one of transmit energy to or receive energy from a second coil and means for absorbing heat from the flexible coil, wherein the means for absorbing heat is configured to deform with the flexible coil.

In a further aspect, the disclosure is directed to a device that includes a flexible coil configured to transmit energy to a second coil, wherein the flexible coil is configured to conform to a non-planar skin surface, a phase change material disposed in one or more shapes selected to deform with the flexible coil and disposed at one or more positions adjacent to the flexible coil, wherein the phase change material is configured to absorb heat from the flexible coil, and a flexible housing configured to encase the flexible coil and the phase change material.

In a further aspect, the disclosure is directed to a method that includes transmitting energy from a flexible primary coil associated with an external recharge device to a secondary coil of an implantable medical device and absorbing heat from the flexible primary coil via a phase change material configured to deform with the flexible coil.

The details of one or more examples are set forth in the accompanying drawings and the description below. Other features, objects, and advantages will be apparent from the description and drawings, and from the claims.

DETAILED DESCRIPTION

Figure 1:
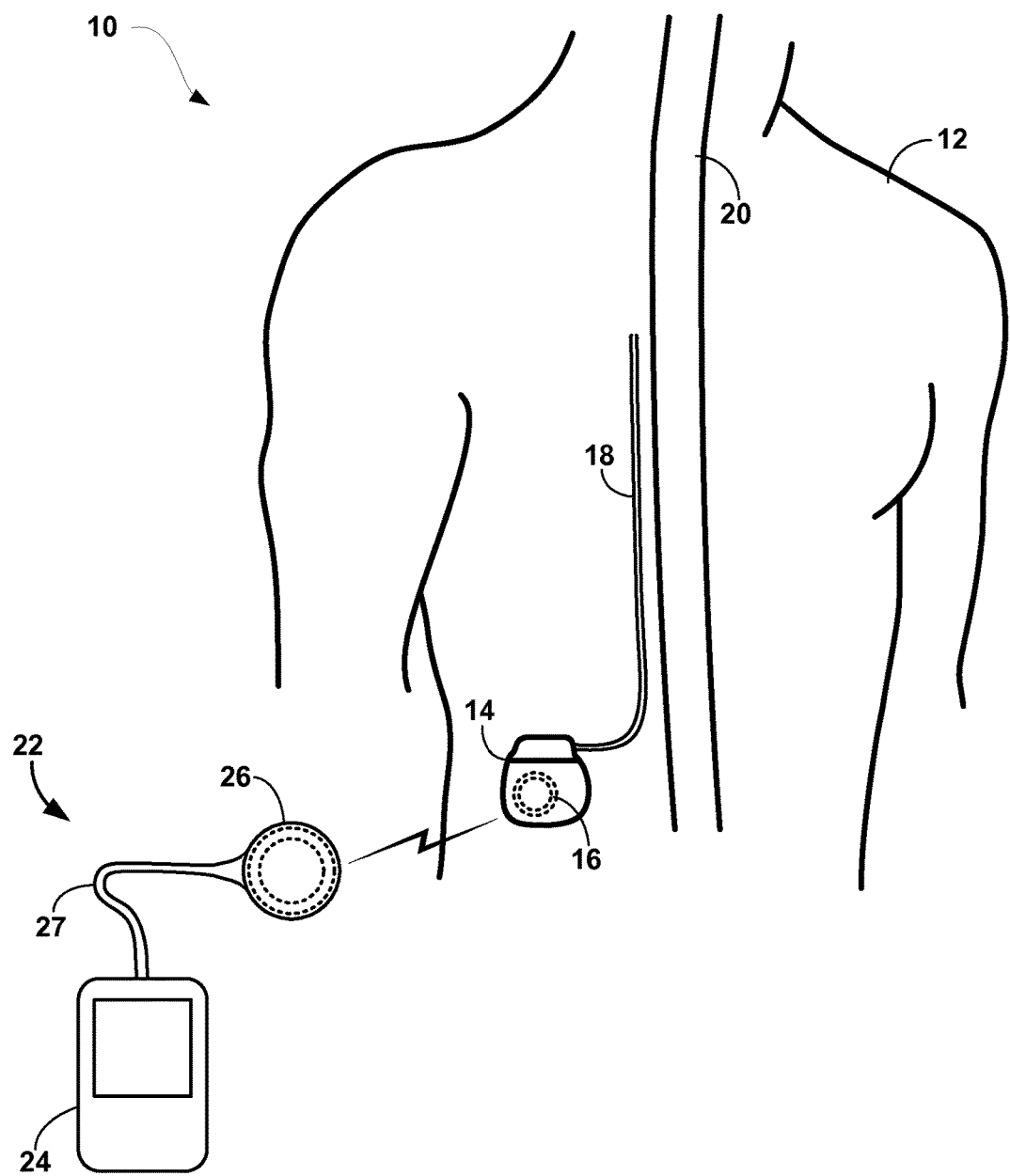
FIG. 1 is a conceptual diagram illustrating an example system that includes an implantable medical device (IMD) and an external charging device that charges a rechargeable power source of the IMD via an energy transfer device including a flexible coil.

This disclosure is generally directed to devices, systems, and techniques for managing heat generated in coils during wireless energy transfer. Typically, inductive coupling, or other wireless energy transfer techniques, may be used to recharge batteries of implantable medical devices (IMDs) and/or transmit information. Inductive coupling may utilize a primary coil of the external charging device to transmit the energy and a secondary coil of the IMD to transcutaneously receive the energy. As an electrical current is generated within the primary coil, the primary coil may increase in temperature, e.g., due to the resistance of the coil. Since the primary coil, and the secondary coil in some examples, may be placed directly against or in close proximity to the skin of the patient, these increases in temperature may become uncomfortable for the patient. The coil may be external of the housing of the IMD or charging device, or in other examples, the coil may be within the housing of the IMD or charging device. The secondary coil of the IMD, however, may be implanted within the patient whether outside or inside of the IMD housing. Not only may these temperatures be uncomfortable, but some patients may prematurely terminate the recharging process or even avoid recharging. Furthermore, typical primary coils may be rigid and uncomfortable when forced against the skin of the patient. In other words, the skin of the patient may be deformed by the primary coil during the recharging process, causing discomfort.

As disclosed herein, a phase change material may be disposed in thermal communication with a flexible coil used in wireless energy transfer. The phase change material may also be configured to deform with the flexible coil. The flexible coil may conform to non-planar skin surfaces of the patient, and the phase change material may absorb heat generated by the flexible coil. The flexible coil may include insulated wire wound in an in-plane spiral. This in-plane spiral may provide a relatively thin coil that can conform to non-planar surfaces to increase comfort to the patient. The flexible coil may be encased by a flexible housing that protects the flexible coil while also allowing the in-plane spiral of wire to bend and flex out of a single plane.

The phase change material generally acts as a heat sink for heat generated by the electrical current in the flexible coil. The heat from the flexible coil may contribute to the heat of fusion of the phase change material as the phase change material changes from a solid state to a fluid state. During this phase change, the material does not increase in temperature and enables the flexible coil to remain at lower temperatures for a longer period of time than otherwise would be possible. In other words, heat generated in the flexible coil may be absorbed by the phase change material during the change in phase to limit temperature increases in the flexible coil. Example phase change materials may include paraffin waxes (e.g., N-eicosane), fatty acid esters, or other materials with a relatively high heat of fusion and melting points at temperatures appropriate for patient use.

The phase change material may also be disposed directly against the wound wire of the flexible coil or separated by a thermally conductive material (e.g., a thermally conductive elastomer). Although the phase change material may be disposed in a disk-shaped volume in thermal communication with a large surface area of the flexible coil, the phase change material may alternatively be disposed in structures, locations, or shapes selected to promote or accommodate the flexibility of the flexible coil. In other words, the phase change material may be configured deform with the flexible coil or otherwise accommodate flexibility of at least a portion of the flexible coil.

When in the solid state, the phase change material may not be easily deformable. Therefore, the phase change material may be contained within channels, tubes, beads, or other volumes at predetermined positions with respect to the flexible coil that facilitate flexibility of the coil. Since smaller cross-sectional thicknesses of the phase change material may promote greater bending (e.g., a lower moment of inertia) than larger cross-sectional thicknesses, the configuration of how the phase change material is disposed within the energy transfer device may at least partially determine the flexibility, or stiffness, of the energy transfer device. In one example, the phase change material may be contained within a plurality of concentric rings on one side of the flexible coil. These configurations (e.g., the volume, shape, and location with respect to the flexible coil) of the phase change material may be selected to accommodate flexibility of the flexible coil. In other words, the phase change material may not inhibit, or only minimally inhibit, the flexibility of the flexible coil.

The flexible coil and the accompanying phase change material may be referred to as an energy transfer device herein. The energy transfer device may also include a flexible housing that encases the flexible coil and the phase change material. In other examples, the flexible housing or multiple housings may be disposed between the flexible coil and the phase change material. The phase change material may be disposed on the side of the flexible coil proximal to patient skin, on the side of the flexible coil distal to patient skin, on opposing sides of the flexible coil, inside the inner diameter of the in-plane spiral of the flexible coil, outside the outer diameter of the in-plane spiral of the flexible coil, or even in between wire turns of the in-plane spiral. In this manner, the energy transfer device may be configured to incorporate the phase change material as needed to manage the temperature of the flexible coil and retain efficient inductive coupling with the other coil.

Although the energy transfer device is generally described as the primary coil external to the patient, the energy transfer device could be utilized as the secondary coil within the patient to utilize the flexibility and heat management characteristics of the energy transfer device described herein. In addition, the energy transfer device may be used outside of the medical field. For example, the energy transfer device may be used in charging of electronic devices such as mobile telephones, tablet computers, media players, or the like, that may benefit from the heat management characteristics of the energy transfer device using a phase change material. The flexible nature of the energy transfer device may allow the energy transfer device to be positioned within or adjacent to devices that may include curves or other non-planar surfaces. Portable electronics and devices operating with minimal active cooling features may benefit from an energy transfer device as described in this disclosure.

FIG. 1 is a conceptual diagram illustrating an example system 10 that includes an implantable medical device (IMD) 14 and an external charging device 22 that charges a rechargeable power source of IMD 14 via energy transfer device 26. Although the techniques described in this disclosure are generally applicable to a variety of medical devices including medical devices such as patient monitors, electrical stimulators, or drug delivery devices, application of such techniques to implantable neurostimulators will be described for purposes of illustration. More particularly, the disclosure will refer to an implantable neurostimulation system for use in spinal cord stimulation therapy, but without limitation as to other types of medical devices.

As shown in FIG. 1, system 10 includes an IMD 14 and external charging device 22 shown in conjunction with a patient 12, who is ordinarily a human patient. In the example of FIG. 1, IMD 14 is an implantable electrical stimulator that delivers neurostimulation therapy to patient 12, e.g., for relief of chronic pain or other symptoms. Generally IMD 14 may be a chronic electrical stimulator that remains implanted within patient 12 for weeks, months, or even years. In the example of FIG. 1, IMD 14 and lead 18 may be directed to delivering spinal cord stimulation therapy. In other examples, IMD 14 may be a temporary, or trial, stimulator used to screen or evaluate the efficacy of electrical stimulation for chronic therapy. IMD 14 may be implanted in a subcutaneous tissue pocket, within one or more layers of muscle, or other internal location. IMD 14 includes a rechargeable power source (not shown) and IMD 14 is coupled to lead 18.

Electrical stimulation energy, which may be constant current or constant voltage based pulses, for example, is delivered from IMD 14 to one or more targeted locations within patient 12 via one or more electrodes (not shown) of lead 18. The parameters for a program that controls delivery of stimulation energy by IMD 14 may include information identifying which electrodes have been selected for delivery of stimulation according to a stimulation program, the polarities of the selected electrodes, i.e., the electrode configuration for the program, and voltage or current amplitude, pulse rate, pulse shape, and pulse width of stimulation delivered by the electrodes. Electrical stimulation may be delivered in the form of stimulation pulses or continuous waveforms, for example.

In the example of FIG. 1, lead 18 is disposed within patient 12, e.g., implanted within patient 12. Lead 18 tunnels through tissue of patient 12 from along spinal cord 20 to a subcutaneous tissue pocket or other internal location where IMD 14 is disposed. Although lead 18 may be a single lead, lead 18 may include a lead extension or other segments that may aid in implantation or positioning of lead 18. In addition, a proximal end of lead 18 may include a connector (not shown) that electrically couples to a header of IMD 14. Although only one lead 18 is shown in FIG. 1, system 10 may include two or more leads, each coupled to IMD 14 and directed to similar or different target tissue sites. For example, multiple leads may be disposed along spinal cord 20 or leads may be directed to spinal cord 20 and/or other locations within patient 12. Lead 18 may carry one or more electrodes that are placed adjacent to the target tissue, e.g., spinal cord 20 for spinal cord stimulation (SCS) therapy.

In alternative examples, lead 18 may be configured to deliver stimulation energy generated by IMD 14 to stimulate one or more sacral nerves of patient 12, e.g., sacral nerve stimulation (SNS). SNS may be used to treat patients suffering from any number of pelvic floor disorders such as pain, urinary incontinence, fecal incontinence, sexual dysfunction, or other disorders treatable by targeting one or more sacral nerves. Lead 18 and IMD 14 may also be configured to provide other types of electrical stimulation or drug therapy (e.g., with lead 18 configured as a catheter). For example, lead 18 may be configured to provide deep brain stimulation (DBS), peripheral nerve stimulation (PNS), or other deep tissue or superficial types of electrical stimulation. In other examples, lead 18 may provide one or more sensors configured to allow IMD 14 to monitor one or more parameters of patient 12. The one or more sensors may be provided in addition to, or in place of, therapy delivery by lead 18.

IMD 14 delivers electrical stimulation therapy to patient 12 via selected combinations of electrodes carried by lead 18. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1, the target tissue for electrical stimulation delivered via lead 18 is tissue proximate spinal cord 20 (e.g., one or more target locations of the dorsal columns or one or more dorsal roots that branch form spinal cord 20. Lead 18 may be introduced into spinal cord 20 via any suitable region, such as the thoracic, cervical or lumbar regions. Stimulation of dorsal columns, dorsal roots, and/or peripheral nerves may, for example, prevent pain signals from traveling through spinal cord 20 and to the brain of the patient. Patient 12 may perceive the interruption of pain signals as a reduction in pain and, therefore, efficacious therapy results. For treatment of other disorders, lead 18 may be introduced at any exterior location of patient 12.

Although lead 18 is described as generally delivering or transmitting electrical stimulation signals, lead 18 may additionally or alternatively transmit electrical signals from patient 12 to IMD 14 for monitoring. For example, IMD 14 may utilize detected nerve impulses to diagnose the condition of patient 12 or adjust the delivered stimulation therapy. Lead 18 may thus transmit electrical signals to and from patient 12.

A user, such as a clinician or patient 12, may interact with a user interface of an external programmer (not shown) to program IMD 14. Programming of IMD 14 may refer generally to the generation and transfer of commands, programs, or other information to control the operation of IMD 14. For example, the external programmer may transmit programs, parameter adjustments, program selections, group selections, or other information to control the operation of IMD 14, e.g., by wireless telemetry or wired connection.

In some cases, an external programmer may be characterized as a physician or clinician programmer if it is primarily intended for use by a physician or clinician. In other cases, the external programmer may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use. In other examples, external charging device 20 may be included, or part of, an external programmer. In this manner, a user may program and charge IMD 14 using one device, or multiple devices.

IMD 14 may be constructed of any polymer, metal, or composite material sufficient to house the components of IMD 14 within patient 12. In this example, IMD 14 may be constructed with a biocompatible housing, such as titanium or stainless steel, or a polymeric material such as silicone or polyurethane, and surgically implanted at a site in patient 12 near the pelvis, abdomen, or buttocks. The housing of IMD 12 may be configured to provide a hermetic seal for components, such as a rechargeable power source. In addition, the housing of IMD 12 may be selected of a material that facilitates receiving energy to charge a rechargeable power source.

As described herein, secondary coil 16 may be included within IMD 14. However, in other examples, secondary coil 16 could be located external to a housing of IMD 14, separately protected from fluids of patient 12, and electrically coupled to electrical components of IMD 14. This type of configuration of IMD 14 and secondary coil 16 may provide implant location flexibility when anatomical for implantable devices is minimal and/or improved inductive coupling between secondary coil 16 and primary coil 26. In any case, an electrical current may be induced within secondary coil 16 to charge the battery of IMD 14 when energy transfer device 26 (e.g., a primary coil) produces a magnetic field is aligned with secondary coil 16. The induced electrical current may first be conditioned and converted by a charging module (e.g., a charging circuit) to an electrical signal that can be applied to the battery with an appropriate charging current. For example, the inductive current may be an alternating current that is rectified to produce a direct current suitable for charging the battery.

The rechargeable power source of IMD 14 may include one or more capacitors, batteries, or components (e.g. chemical or electrical energy storage devices). Example batteries may include lithium-based batteries, nickel metal-hydride batteries, or other materials. The rechargeable power source may be replenished, refilled, or otherwise capable of increasing the amount of energy stored after energy has been depleted. The energy received from secondary coil 16 may be conditioned and/or transformed by a charging circuit. The charging circuit may then send an electrical signal used to charge the rechargeable power source when the power source is fully depleted or only partially depleted.

Charging device 22 may be used to recharge the rechargeable power source within IMD 14 implanted in patient 12. Charging device 22 may be a hand-held device, a portable device, or a stationary charging system. In any case, charging device 22 may include components necessary to charge IMD 14 through tissue of patient 12. Charging device 22 may include housing 24 and energy transfer device 26. Housing 24 may enclose operational components such as a processor, memory, user interface, telemetry module, power source, and charging circuit configured to transmit energy to secondary coil 16 via energy transfer device 26. Although a user may control the recharging process with a user interface of charging device 22, charging device may alternatively be controlled by another device (e.g., an external programmer).

Charging device 22 and IMD 14 may utilize any wireless power transfer techniques that are capable of recharging the power source of IMD 14 when IMD 14 is implanted within patient 14. In one example, system 10 may utilize inductive coupling between primary (e.g., energy transfer device 26) and secondary coils (e.g., secondary coil 16) of charging device 22 and IMD 14. In inductive coupling, charging device 22 is placed near implanted IMD 14 such that the primary coil of charging device 22 is aligned with secondary coil 16 of IMD 14. Charging device 22 may then generate an electrical current in the primary coil based on a selected power level for charging the rechargeable power source of IMD 14. When the primary and secondary coils are aligned, the electrical current in the primary coil may magnetically induce an electrical current in the secondary coil within IMD 14. Since the secondary coil is associated with and electrically coupled to the rechargeable power source, the induced electrical current may be used to increase the voltage, or charge level, of the rechargeable power source. Although inductive coupling is generally described herein, any type of wireless energy transfer may be used to transfer energy between charging device 22 and IMD 14.

Energy transfer device 26 may include a flexible coil (not shown in FIG. 1) and phase change material (not shown in FIG. 1). The flexible coil may be constructed of a wire wound in an in-plane spiral (e.g., a disk-shaped coil). The flexible coil may include wires that electrically couple the flexible coil to a power source and a charging module configured to generate an electrical current within the flexible coil. Energy transfer device 26 may also include a flexible housing that encases the flexible coil, and in some examples, the phase change material. Energy transfer device 26 may be external of housing 24 such that energy transfer device 25 can be placed on the skin of patient 12 proximal to IMD 14. In this manner, energy transfer device 26 may be tethered to housing 24 using cable 27 or other connector that may be between approximately a few inches and several feet in length. In other examples, energy transfer device 26 may be disposed on the outside of housing 24 or even within housing 24. Energy transfer device 26 may thus not be tethered to housing 22 in other examples. In other examples, energy transfer device 26 may be disposed within housing 24.

Energy transfer device 26 may also include phase change material that absorbs heat generated in the flexible coil during then energy transfer process. As charging device 22 generates an electrical current within the flexible coil, the current may produce heat that increases the temperature of the flexible coil. When energy transfer device 26 is in close proximity to the skin of patient 12, this increase in temperature may be uncomfortable to patient 12. In other words, energy transfer device 26 may feel warm to the touch. This increase in temperature may cause patient 12 to shift energy transfer device 26 to a different location on the skin, remove energy transfer device 26 from the skin, or even discontinue or delay the charging session. Therefore, increased temperatures from energy transfer device 26 may lead to operational shortcomings of IMD 14, such as reduced operational times between charging sessions, in addition to patient discomfort.

The phase change material may be included in energy transfer device 26 to manage the temperature of energy transfer device 26. The phase change material may be any compound or substance selected to change phases (e.g., change from a solid state to a liquid state) at a temperature within the operating temperatures of the flexible coil. Generally, the melting point of the phase change material may be lower than a temperature that would be uncomfortable to patient 12. For example, the phase change material may be selected to have a melting point between approximately 15 degrees Celsius and 50 degrees Celsius. More specifically, the phase change material may have a melting point between approximately 25 degrees Celsius and 45 degrees Celsius. In another example, the phase change material may have a melting point between approximately 35 degrees Celsius and 43 degrees Celsius.

In one example, it may be desirable to limit the temperature of energy transfer device 26, and the adjacent skin, to be less than or equal to approximately 39 degrees Celsius. Therefore, the phase change material may be selected with a melting point at or near the desired temperature limit. A desired melting point of the phase change material may thus be just below approximately 39 degrees Celsius, such as between approximately 35 degrees Celsius and approximately 38 degrees Celsius. The heat of fusion of the phase change material may thus provide a relatively large heat sink that may help to limit the rise in temperature of the skin above the desired temperature limit. The mass of the phase change material may be selected to achieve desired temperatures of energy transfer device 26. With higher masses of the phase change material, energy transfer device 26 may remain at the melting point of the phase change material for longer periods of time and limit the temperature of energy transfer device 26.

In this manner, heat from the flexible coil may contribute to the heat of fusion of the phase change material to delay higher temperatures in energy transfer device 26. After the phase change material has changed to from the solid state to the liquid state, the ability of the phase change material to act as a heat sink may be reduced. However, the phase change material may be subjected to many cycles of changing phases. After the charging session, the flexible coil will cool along with the phase change material. The phase change material may change back to the solid state from the higher temperature liquid state. Subsequently, the heat of fusion of the phase change material may again function as a heat sink for the flexible coil.

The amount of heat the phase change material can absorb is also dependent upon the type of material selected, the mass of the material, and thermal communication between the flexible coil and the phase change material. Although a greater mass of material may absorb a greater amount of heat from the flexible coil, energy transfer device 26 may become less flexible and with a greater mass of the phase change material. The phase change material may be in thermal communication with the flexible coil when there is a minimally resistive path for heat between the phase change material and the flexible coil. In this manner, the phase change material may be in thermal communication with the flexible coil when the phase change material may is disposed in direct contact with the flexible coil or separated from the flexible coil with a thermally conductive material (e.g., a thermally conductive elastomer or a deformable metal alloy). The phase change material may not be in thermal communication with the flexible coil when an insulator (e.g., a gas, a vacuum, or a thermally insulative material) is disposed between the phase change material to reduce the rate of heat transferred from the flexible coil to the phase change material.

In some examples, two or more different types of phase change materials may be disposed within energy transfer device 26. These different materials may be disposed at different locations of energy transfer device 26 or commingled across the surface of the flexible coil. Since the different materials may include different melting points and different heats of fusion, the temperature profile of energy transfer device 26 over time may be manipulated. In other words, a phase change material having a lower melting point may delay changes in temperature at a lower temperature while a different phase change material having a higher melting point may delay changes in temperature at a higher temperature. This temperature profile may be selected to provide a more comfortable experience for patient 12. For example, a specific phase change material may be selected to absorb typical temperature spikes during energy transfer, reduce the initial temperature rate increase during energy transfer, and/or reduce the rate of temperature increase near the end of charging sessions.

The phase change material may be selected from any variety of materials having properties sufficient to perform the functions described herein. For example, the phase change material may be a paraffin wax, a fatty acid, ester (carboxylic acid), inorganic materials such as salt hydrates or sodium hydrogen phosphate, or other compounds. The paraffin wax may be a saturated alkane having between 19 and 23 carbon atoms that have approximate melting points in a desired range. Example paraffin waxes may include nonadecane ($C_{19}H_{40}$; approximate melting point of 32.0 degrees Celsius), eicosane or N-eicosane ($C_{20}H_{42}$; approximate melting point of 36.4 degrees Celsius), heneicosane ($C_{21}H_{44}$; approximate melting point of 40.4 degrees Celsius), docosane ($C_{22}H_{46}$; approximate melting point of 44.4 degrees Celsius), or tricosane ($C_{23}H_{48}$; approximate melting point of 47.4 degrees Celsius). In one example, the phase change material selected for energy transfer device 26 may include eicosane. In some examples, the phase change material may include both eicosane and heneicosane. In this manner, different phase change materials may be included in energy transfer device 26 either in combination or at separate locations in energy transfer device 26.

The amount of phase change material included within energy transfer device 26 may be selected based on the power transferred by energy transfer device 26, the material of wire for the flexible coil, the amount of time needed for energy transfer, and the desired temperature limit for energy transfer device 26. The mass of phase change material needed for energy transfer device 26 may also be based on the type of material selected. Generally, energy transfer device 26 may include between approximately 1.0 gram of phase change material and 100 grams of phase change material. In one example, an energy transfer device 26 with a flexible coil having a 10 centimeter diameter and a thickness of approximately 4.5 millimeters may include approximately 10 grams of phase change material.

As described herein, energy transfer device 26 may include a flexible coil and a phase change material. The flexible coil may be configured to at least one of transmit energy to or receive energy from secondary coil 16, and the phase change material may be in thermal communication with at least a portion of the flexible coil such that the phase change material is configured to absorb heat from the flexible coil. The phase change material (e.g., any material selected to change phases at a temperature generated by the flexible coil) may be a means for absorbing heat from the flexible coil.

In some examples, the phase change material may be disposed in one or more shapes selected to accommodate flexibility of the flexible coil and disposed at one or more positions adjacent to the flexible coil. In other words, the pattern, shape, and volume of the phase change material may be configured to promote flexibility of energy transfer device 26 in one or more directions and to the same degree as that of the flexible coil (e.g., the phase change material may be configured to deform with the flexible coil). In this manner, the phase change material size and/or shape may not inhibit (or only minimally inhibit) flexibility of the flexible coil. This configuration of the phase change material may be directed to when the phase change material is in the solid state (e.g., when temperatures of energy transfer device 26 below the melting point of the phase change material).

Energy transfer device 26 may also include a flexible housing (not shown in FIG. 1) configured to encase the flexible coil and the phase change material. The flexible housing, e.g., a means for encasing the flexible coil, may be constructed of a flexible material that does not restrict the flexibility of the flexible coil. In other words the flexible housing may have an elasticity greater than or equal to the elasticity of the flexible coil. The flexible coil, and the entire energy transfer device 26, may be configured to conform to a non-planar skin surface such that the flexible housing is configured to deform with the flexible coil.

The flexible housing may encase the flexible coil and the phase change material within a single chamber or, alternatively, the flexible housing may encase the flexible coil in a separate chamber than the chamber that contains the phase change material. In examples in which the flexible coil and the phase change material are separated, the flexible housing may be constructed of a thermally conductive material to transfer heat between the flexible coil and the phase change material. The thermally conductive material of the flexible housing may include polymers (e.g., thermally conductive elastomers), woven composites, deformable alloys, or other materials that allow the transfer of heat. In some examples, the flexible housing may include one or more channels configured to contain the phase change material. These channels may contain the phase change material to predetermined locations of energy transfer device 26 to prevent pooling of the phase change material in the liquid state and retain selected shapes and positions of the phase change material in the solid state.

In some examples, energy transfer device 26 may include a containment structure comprising one or more channels configured to contain the phase change material. The containment structure may then be encased by the flexible housing. The channels, in some examples, may be configured as a plurality of cavities that each contain a portion of the phase change material. The containment structure may include two mating portions that are filled with the phase change material and, when combined, contain the phase change material in the channels of the two mating portions. Alternatively, a film may be applied to a surface of the containment structure to retain the phase change material within the one or more channels of the containment structure. In this example, the film may also be configured to contact the flexible coil and transfer heat to the phase change material. The containment structure may be constructed with a material having elastic properties or with a shape that facilitates bending such that the containment structure also accommodates flexibility of the flexible coil.

In other examples, energy transfer device 26 may include one or more flexible tubes configured to contain the phase change material at predetermined locations with respect to the flexible coil. These flexible tubes may be used to contain the phase change material such that the phase change material is disposed within the one or more flexible tubes. The flexible tubes may be constructed of a polymer with a higher melting point temperature than temperatures to which energy transfer device 26 would normally be exposed. In one example, the flexible tubes may be constructed of a thermally conductive elastomer. In other examples, the tube used may not be flexible. Although the tube may be rigid or generally inflexible, the shape of the tube may still promote deformation of energy transfer device 26 in one or more directions.

Alternatively, or in addition to other containment techniques, energy transfer device 26 may include a woven material to limit the movement of fluid state phase change material. The woven material may be constructed of a natural or synthetic fiber that promotes wicking of the phase change material in the liquid state. Instead of pooling within energy transfer device 26, the liquid phase change material may adhere to the woven material. Therefore, the phase change material may be placed in contact with the woven material to retain the phase change material in thermal communication with the flexible coil. Although the woven material may be only encased by the flexible housing, the woven material may also be contained by a bladder, flexible tube, or other cavity.

In another alternative example, the phase change material may be encapsulated in a plurality of beads or capsules distributed adjacent at least one surface of the flexible coil. Each of these beads may be isolated locations of phase change material. Each of the beads may include phase change material covered with a thermally conductive material, such as an inert and chemically stable polymer. The beads may promote flexibility of energy transfer device 26 because each bead may be a relatively small volume compared with the flexible coil. The beads may be shaped as spheres, ovoids, cubes, or other shapes selected to be contained within the flexible housing of energy transfer device 26. The beads may generally have an outside diameter between approximately 20.0 micrometers and 5.0 millimeters. In other examples, the outside diameter of the beads may be smaller than 20.0 micrometers or greater than 5.0 millimeters. The dimensions of the beads may be selected based on the total mass or volume of phase change material required and/or the dimensions of energy transfer device 26.

The flexible coil may be formed by one or more coils of wire. In one example the coil is formed by a wire wound into a spiral within a single plane (e.g., an in-plane spiral). This in-plane spiral may be constructed with a thickness equal to the thickness of the wire, and the in-plane spiral may be capable of transferring energy with another coil. In other examples, the coil may be formed by winding a coil into a spiral bent into a circle. However, this type of coil may not be as thin as the in-plane spiral. With any flexible coil, the phase change material may be disposed adjacent to the coil in a variety of different configurations.

In one example, the phase change material may be disposed in a disk-shaped volume of a second plane adjacent to the in-plane spiral. The disk-shaped volume of phase change material may be a solid volume of phase change material approximately the same diameter of the in-plane spiral, and the second plane may be parallel with the in-plane spiral. The phase change material may alternatively be disposed in a plurality of concentric rings in a second plane adjacent to the in-plane spiral. However, the phase change material may instead be formed as a spiral tube of phase change material in the second plane adjacent to the in-plane spiral.

The phase change material may be disposed in a second plane different than the in-plane spiral flexible coil in additional configurations. For example, the phase change material may be disposed in a zigzag pattern adjacent to the in-plane spiral. The zigzag pattern may have radial, circumferential, or transverse sections to create the zigzag pattern. These zigzag patterns may be configured to promote curvature of the flexible coil in predetermined directions (e.g., radial curvature, circumferential curvature, or transverse curvature. In other examples, the phase change material may be disposed in a plurality of cavities in the second plane.

In another example, the phase change material may be disposed within the in-plane spiral as at least one phase change material spiral. In other words, the phase change material may be formed into a spiral in the same plane of the flexible coil. In other examples, the phase change material may be disposed as a coil or rings inside the inner diameter of the in-plane spiral and/or outside the outer diameter of the in-plane spiral.

Although the phase change material may only be disposed on once side of the flexible coil, the phase change material may be disposed on opposing sides, e.g., both sides, of the flexible coil in other examples. Energy transfer device 26 may include one configuration of the phase change material or multiple different configurations of the phase change material. For example, a plurality of concentric rings of phase change material may be disposed on one side of the flexible coil and the phase change material may be disposed in a plurality of cavities on an opposing side of the flexible coil. In addition, the thickness and/or mass of phase change material may be different on one side of the flexible coil from the other side of the flexible coil.

Energy transfer device 26 may include phase change material disposed such that the phase change material is between skin of patient 12 and the flexible coil. Alternatively, energy transfer device 26 may include the phase change material disposed on the opposite side of the flexible coil than the skin of patient 12. In addition, the phase change material may be disposed on both sides of the flexible coil. The position of phase change material within energy transfer device 26 with respect to the flexible coil may be selected based on the specific purpose of system 10.

Figure 2A:
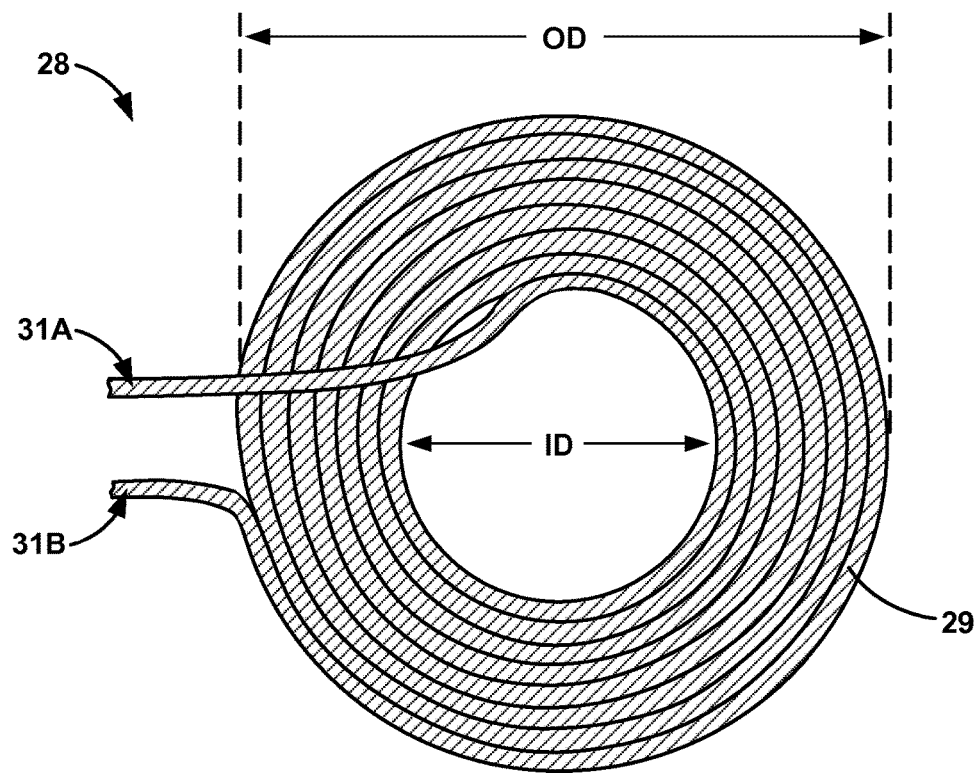
FIG. 2A is a conceptual diagram of an example flexible coil of an energy transfer device.

FIG. 2A is a conceptual diagram of an example flexible coil 28 of energy transfer device 26 of FIG. 1. Flexible coil 28 may be formed of wire 29 wound into a spiral, e.g., an in-plane spiral, with an inner diameter (ID) and an outer diameter (OD). Wire 29 may have a selected number of turns directed to the characteristics of energy transfer with another coil, e.g., secondary coil 16 of IMD 14. In general, wire 29 may have as few as 2 turns and as many as several hundred turns to create flexible coil 28. Flexible coil 28 may electrically couple to a charging module of charging device 22 with wire ends 31A and 31B that may be of any length as needed to couple with the charging module. Although wire 29 may be wound in a single layer, other examples of flexible coil 28 may include two or more layers of wire 29 wound in a spiral or circle. Flexible coil 28 with multiple layers of wire 29 may also be considered to be an in-plane spiral if wire 29 is spiral wound.

Wire 29 may be constructed of any electrically conductive material sufficient to transfer energy during inductive coupling, for example. Example materials for wire 29 may include copper, silver, gold, aluminum, nickel, or some alloy of two or more materials. Wire 29 may generally have a thickness between approximately 0.5 millimeters (mm) and 10 mm. In one example, wire 29 may have a thickness of approximately 4.5 mm. In general, the OD of flexible coil 28 may be between approximately 2.0 centimeters (cm) and 25 cm. The ID of flexible coil 28 may generally be between approximately 0.5 cm and 20 cm. In one example, flexible coil 28 may have an OD of approximately 10 cm and an ID of approximately 5 cm. In other examples, the dimensions of flexible coil 28 and wire 29 may be outside of these ranges for certain applications. In some examples, wire 29 may be covered in insulation that coats the wire. In this manner, insulation may reduce electrical current transfer between adjacent windings of wire 29.

Figure 2B:
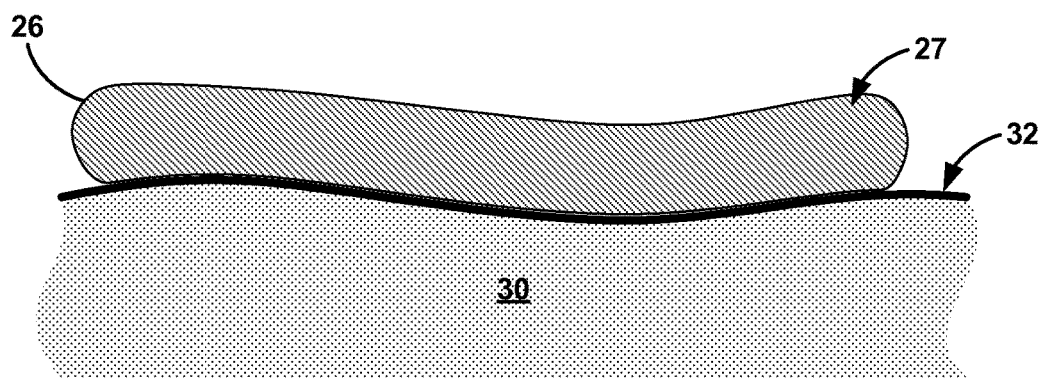
FIG. 2B is a conceptual diagram of an example energy transfer device of FIG. 1 conformable to a non-planar skin surface.

FIG. 2B is a conceptual diagram of an example energy transfer device 26 of FIG. 1 conformable to a non-planar skin surface 32. As shown in FIG. 2B, skin 30 includes a skin surface 32 that may not be in a single plane. In other words, skin surface 32 may have undulations, curves, and other non-flat surfaces. Therefore, energy transfer device 26 may be flexible such that the device can conform to skin surface 32. An in-plane spiral of wire 29, as shown in FIG. 2A of flexible coil 28, may allow flexible coil 28 and energy transfer device 26 to bend and flex as needed.

In this manner, the flexible coil of energy transfer device 26 may be configured to conform to non-planar skin surface 32. The flexible housing of energy transfer device 26 may also be configured to deform with the flexible coil. In addition, the phase change material within energy transfer device 26 may be disposed in one or more shapes selected to accommodate flexibility of the flexible coil. Flexible housing 27 may also be configured to encase the flexible coil and the phase change material and conform to skin surface 32 with the flexible coil.

Figure 3A:
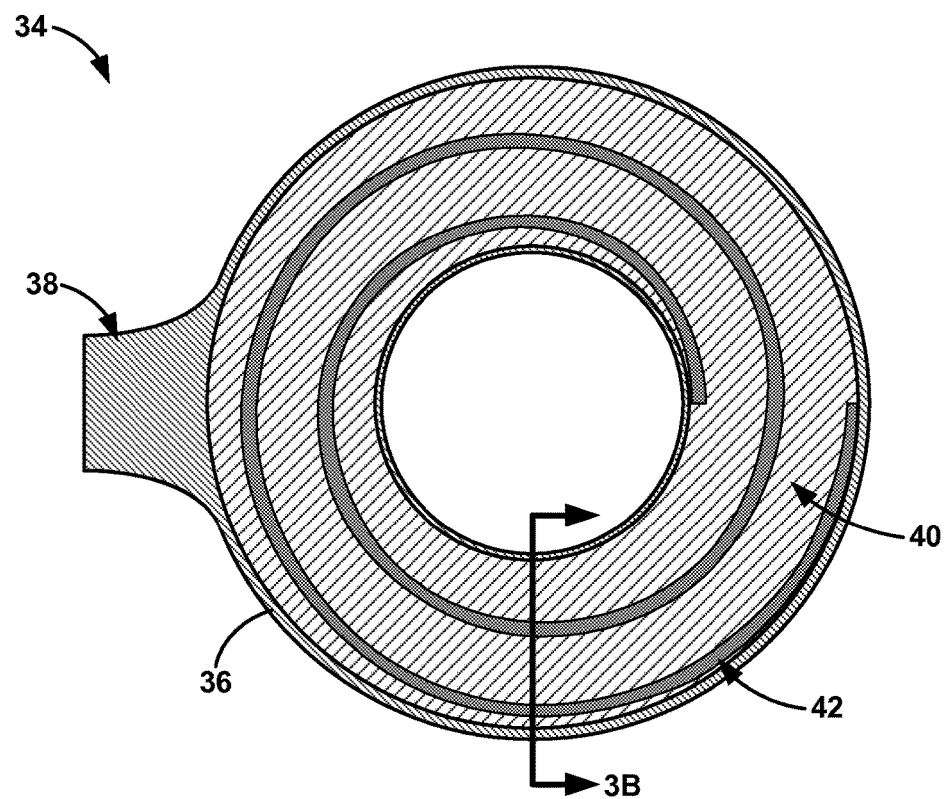
FIGS. 3A and 3B are cross-sectional top and side views of a phase change material disposed in a phase change material spiral within the in-plane spiral of a flexible coil.
Figure 3B:
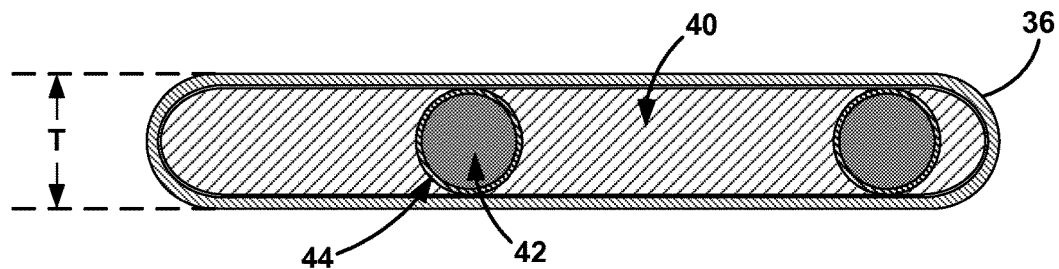

FIGS. 3A and 3B are cross-sectional top and side views of phase change material 42 disposed as a phase change material spiral within the in-plane spiral of flexible coil 40. Energy transfer device 34 is an example of energy transfer device 26 of FIG. 1. As shown in FIG. 3A, energy transfer device 34 includes flexible coil 40, phase change material 42, flexible housing 36, and connector portion 38. FIG. 3A shows energy transfer device 34 with the top of flexible housing 36 removed to expose flexible coil 40 and phase change material 42 within flexible coil 40. Flexible coil 40 is shown as a solid component in FIGS. 3A and 3B for ease of illustration, but flexible coil 40 may be an in-plane spiral of multiple wire turns similar to that of flexible coil 28 of FIG. 2A. The wire of flexible coil 40 may extend from flexible coil 40 to a charging circuit via connector portion 38. In other examples, separate wires may be coupled to flexible coil 40 to transfer or receive electrical current from the charging circuit. Flexible coil 40 and the connection of flexible coil 40 to a charging circuit may be similar to the flexible coils of energy transfer devices 50, 60, 80, 90, 100, 120, 140, and 160 described herein.

Energy transfer device 34 includes phase change material 42 disposed within the in-plane spiral of flexible coil 40. In this manner, phase change material 42 may form a phase change material spiral that turns with the wire of flexible coil 40. In other words, phase change material 42 and the wire of flexible coil 40 may be disposed side-by-side and wound together such that phase change material 42 may be imbedded with the in-plane spiral of flexible coil 40. Phase change material 42 may take the place of windings in some examples or merely interleaved between wire turns. This configuration may allow energy transfer device 34 to be constructed with minimal thickness. Although phase change material 42 is illustrated with two turns within energy transfer device 34, phase change material 42 may include a similar number of turns as the wire of flexible coil 40.

FIG. 3B is an illustration of a cross-section of energy transfer device 34 indicated by section 3B in FIG. 3A. Flexible coil 40 is shown with phase change material 42 embedded within the in-plane spiral of flexible coil 40. The thickness T of energy transfer device 34 may be similar to that of the thickness of the wire in flexible coil 40. For example, thickness T may be between approximately 0.5 millimeters (mm) and 10 mm. In one example, the thickness T may be approximately 5.0 mm. Flexible housing 36 also encases both flexible coil 40 and phase change material 42.

Energy transfer device 34 may also include one or more flexible tubes, such as flexible tube 44. Flexible tube 44 may be configured to contain phase change material 42 at the predetermined location with respect to flexible coil 40. In this manner, phase change material 42 may be disposed within flexible tube 44 such that flexible tube 44 may be a casing for the phase change material. Flexible tube 44 may be constructed of a thermally conductive elastomer that is chemically inert to phase change material 42 and chemically stable. Flexible tube 44 may function to retain phase change material 42 if phase change material 42 changes to the liquid state.

In some examples, energy transfer device 34 may include a woven material placed in contact with phase change material 42. The woven material may be used to retain phase change material 42 in thermal communication with flexible coil 40 because the phase change material 42 may wick to the woven material when in the liquid state. This woven material may be used in addition to, or instead of, flexible tube 44.

In other examples, energy transfer device 34 may incorporate phase change material 42 encapsulated in a plurality of beads distributed adjacent at least one surface of flexible coil 40. These beads of phase change material may be disposed within the in-plane spiral of flexible coil 40, but individual beads may take the place of the tubes of phase change material. Each of the beads may include a polymer coating around phase change material 42 to retain the phase change material in the shape of the bead. In this manner, both flexible tube 44 and beads may be means for containing phase change material 42 at predetermined locations with respect to flexible coil 40. In alternative examples, flexible housing 36 may include ridges or channels that extend across the thickness of energy transfer device 34 to functionally contain phase change material 42 and separate phase change material 42 from flexible coil 40.

Figure 4A:
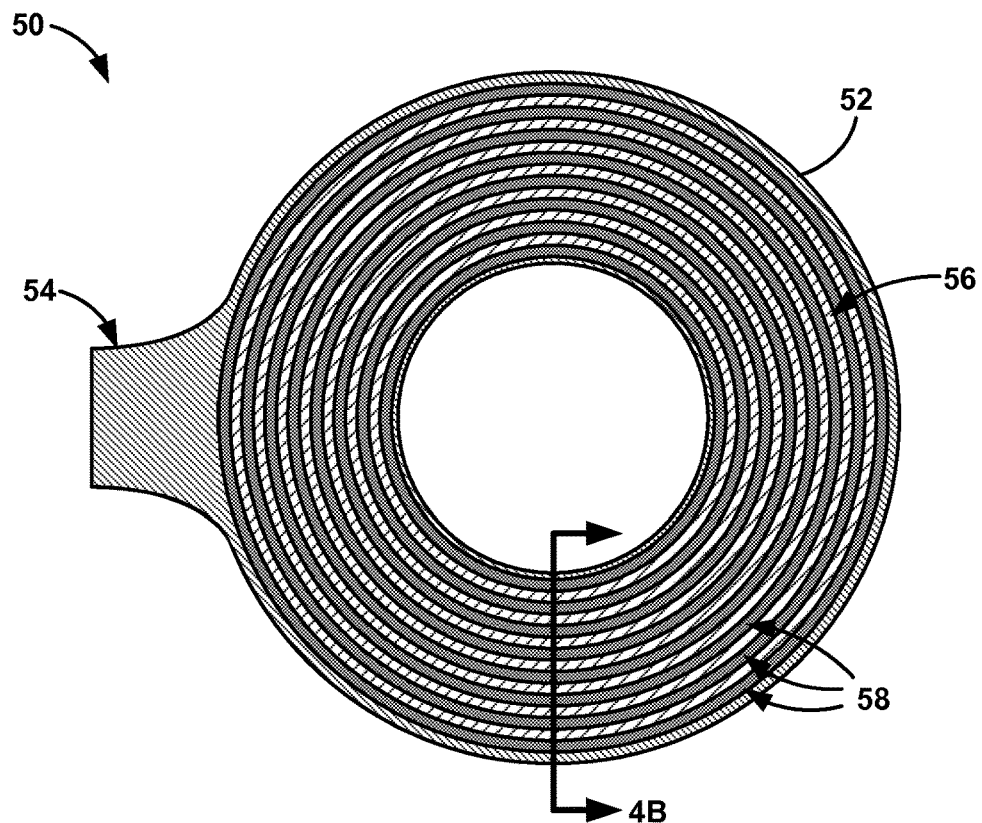
FIGS. 4A and 4B are cross-sectional top and side views of a phase change material disposed in a plurality of concentric rings adjacent to the in-plane spiral of a flexible coil.
Figure 4B:
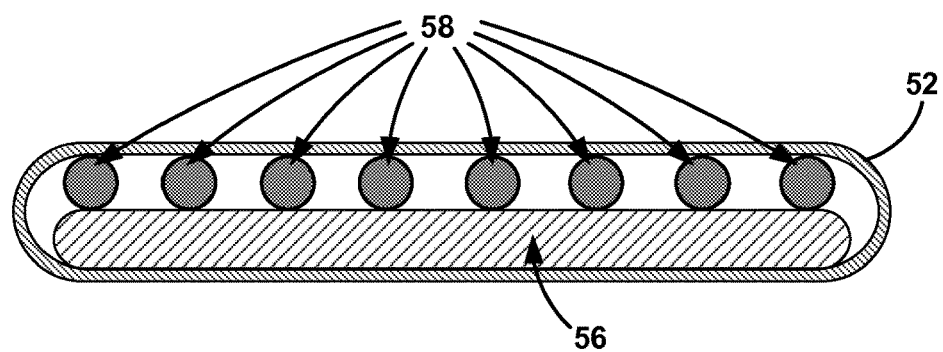

FIGS. 4A and 4B are cross-sectional top and side views of phase change material 58 disposed in a plurality of concentric rings adjacent to the in-plane spiral of flexible coil 56. Energy transfer device 50 is an example of energy transfer device 26 of FIG. 1. As shown in FIG. 4A, energy transfer device 50 includes flexible coil 56, phase change material 58, flexible housing 52, and connector portion 54. FIG. 4A shows energy transfer device 50 with the top of flexible housing 52 removed to expose flexible coil 56 and phase change material 58 on top of, or adjacent to, flexible coil 56. Flexible coil 56 is shown as a solid component in FIGS. 4A and 4B for ease of illustration, but flexible coil 56 may be an in-plane spiral of wire similar to that of flexible coil 28 of FIG. 2A.

Energy transfer device 50 includes phase change material 58 disposed in a plurality of concentric rings in a plane adjacent to the in-plane spiral of flexible coil 56. The concentric rings may be separated (e.g., by a void or other material) or in contact with each other. The concentric rings of phase change material 58 may reside flat against flexible coil 56 to promote thermal communication between flexible coil 56 and phase change material 58. In the example of FIG. 4A, energy transfer device 50 includes eight rings of phase change material 58. Phase change material 58 may be disposed in as few as one ring in another example or as many as 20 or more concentric rings on other examples. Alternatively, phase change material 58 may be disposed as a continuous spiral instead of distinct concentric circles. Phase change material 58 may be disposed in concentric rings on one side of flexible coil 56 or on both opposing sides of flexible coil 56 in other examples.

FIG. 4B is an illustration of a cross-section of energy transfer device 50 indicated by section 4B in FIG. 4A. Flexible coil 56 is shown with phase change material 58 on top of and adjacent to flexible coil 56. The thickness of energy transfer device 50 may be greater than the thickness of the wire in flexible coil 56 because energy transfer device 50 includes a layer of phase change material 58. Flexible housing 52 also encases both flexible coil 56 and phase change material 58. Although the spaces between the rings of phase change material 58 may be filled with air or other gas, the spaces may instead be filled with a thermally conductive fluid or deformable material.

Similar to energy transfer device 34 of FIG. 3B, energy transfer device 50 may also include one or more flexible tubes, beads, or a woven material to contain phase change material 58 at predetermined locations with respect to flexible coil 56. In some examples, flexible housing 52 may include one or more channels configured to contain phase change material 58. The channels may be formed by ridges that extend towards flexible coil 56. In other examples, energy transfer device 50 may include a containment structure that includes one or more channels configured to contain phase change material 58. A film may then be applied to a surface of the containment structure to retain phase change material 58 within the one or more channels. The film may be thermally conductive and contact flexible coil 56. Alternative to the film, the containment structure may include multiple portions that separate to receive phase change material 58 and seal to retain the phase change material within energy transfer device 50.

Figure 5A:
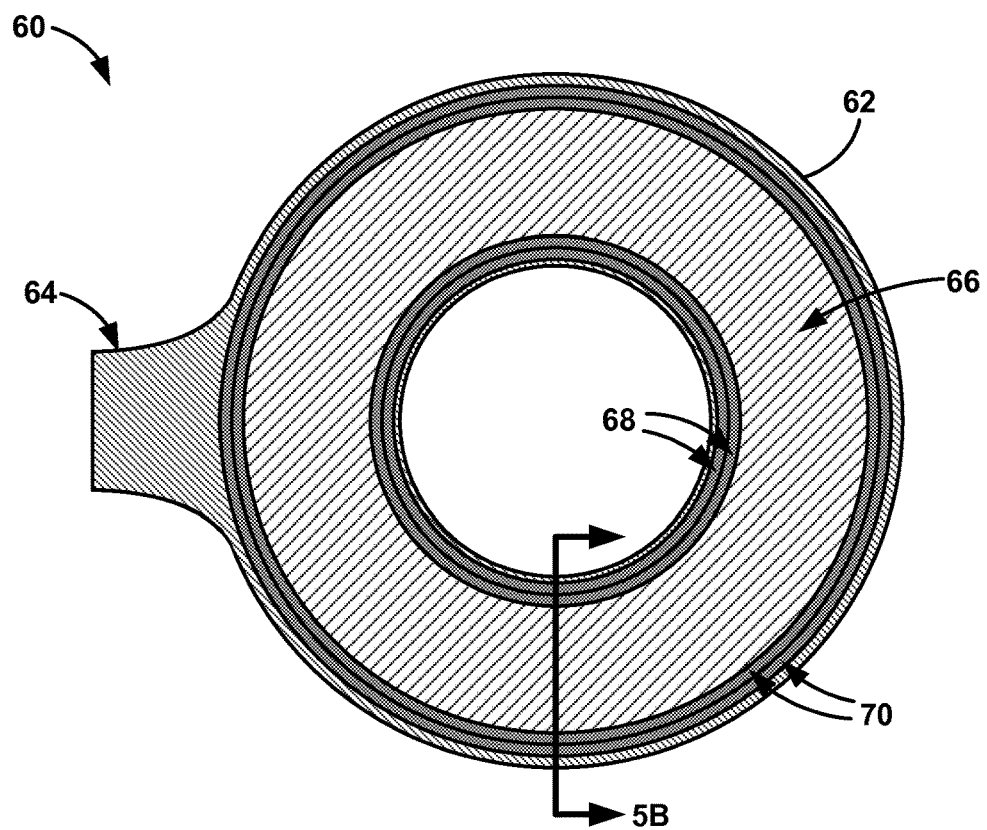
FIGS. 5A and 5B are cross-sectional top and side views of a phase change material disposed inside an inner diameter and outside an outer diameter of the in-plane spiral of a flexible coil.
Figure 5B:
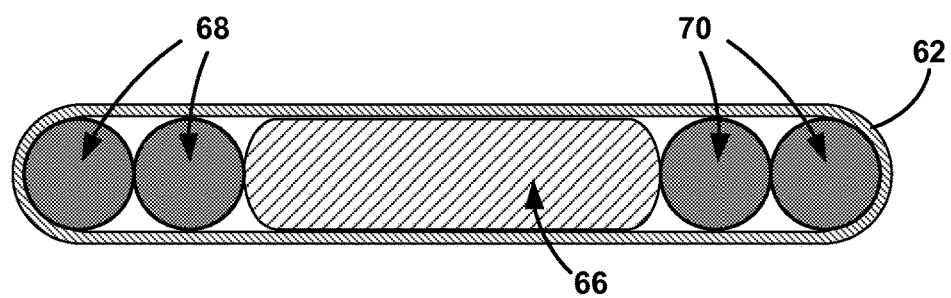

FIGS. 5A and 5B are cross-sectional top and side views of phase change material disposed inside an inner diameter and outside an outer diameter of the in-plane spiral of flexible coil 66. Energy transfer device 60 is an example of energy transfer device 26 of FIG. 1. As shown in FIG. 5A, energy transfer device 60 includes flexible coil 66, flexible housing 62, connector portion 54, and phase change material disposed in inner rings 68 and outer rings 70. FIG. 5A shows energy transfer device 60 with the top of flexible housing 62 removed to expose flexible coil 66 and the phase change material adjacent flexible coil 66 in inner rings 68 and outer rings 70. Flexible coil 66 is shown as a solid component in FIGS. 5A and 5B for ease of illustration, but flexible coil 56 may be an in-plane spiral of wire similar to that of flexible coil 28 of FIG. 2A.

Energy transfer device 60 includes phase change material disposed in a plurality of rings in the same plane as the in-plane spiral of flexible coil 66. More specifically, the phase change material is disposed within rings inside the inner diameter of the in-plane spiral coil and outside the outer diameter of the in-plane spiral coil. Inner rings 68 include the phase change material disposed inside the inner diameter of flexible coil 66. In addition, outer rings 70 include the phase change material disposed outside the outer diameter of flexible coil 66. Although FIGS. 5A and 5B illustrates two inner rings 68 and two outer rings 70, other examples of energy transfer device 60 may include a single inner ring and a single outer ring, or more than two inner and outer rings. In addition, the number of inner rings 68 may be different than the number of outer rings 70. In other examples, a spiral, or coil, of phase change material may be disposed in place of inner rings 68 and/or outer rings 70.

FIG. 5B is an illustration of a cross-section of energy transfer device 60 indicated by section 5B in FIG. 5A. Flexible coil 66 is shown with phase change material disposed in inner rings 68 and outer rings 70 to the sides of and adjacent to flexible coil 66. The thickness of energy transfer device 60 may be similar to the thickness of the wire in flexible coil 66 because energy transfer device 60 does not require additional layers of phase change material. Flexible housing 62 also encases both flexible coil 66 and the phase change material of inner rings 68 and outer rings 70. Although the spaces between rings 68 and 70 and flexible coil 66 may be filled with air or other gas, the spaces may instead be filled with a thermally conductive fluid or deformable material.

Similar to energy transfer device 34 of FIG. 3B, energy transfer device 60 may also include one or more flexible tubes, beads, or a woven material to contain the phase change material if rings 68 and 70 at predetermined locations with respect to flexible coil 66. In some examples, flexible housing 62 may include one or more channels configured to contain the phase change material. In other examples, a containment structure and/or a film may be used to contain the phase change material at the inner and outer diameter locations with respect to flexible coil 66.

Figure 6A:
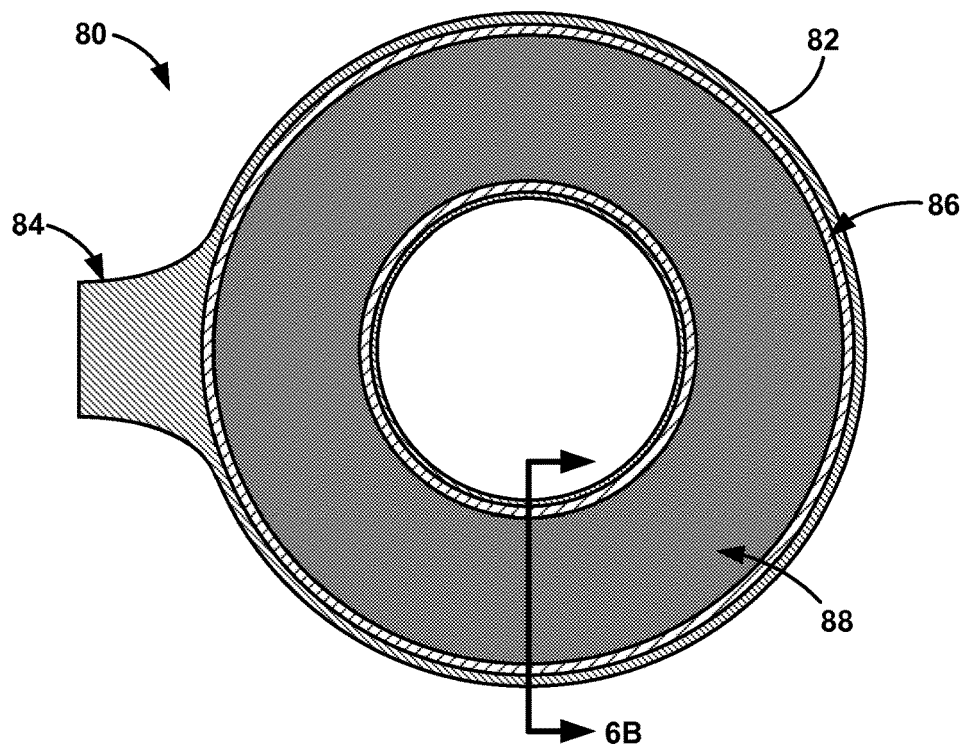
FIGS. 6A, 6B, and 6C are cross-sectional top and side views of a phase change material disposed in a disk-shaped volume adjacent to the in-plane spiral of a flexible coil.
Figure 6B:
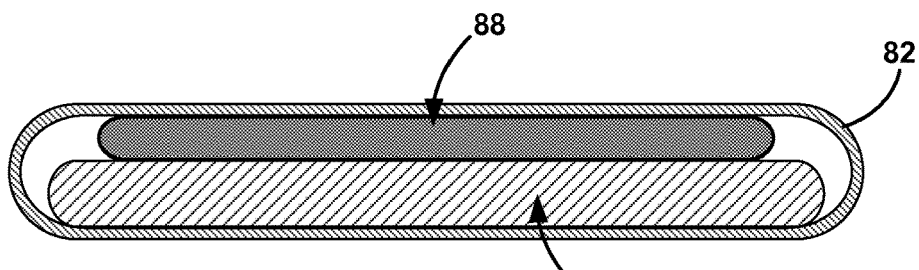
Figure 6C:
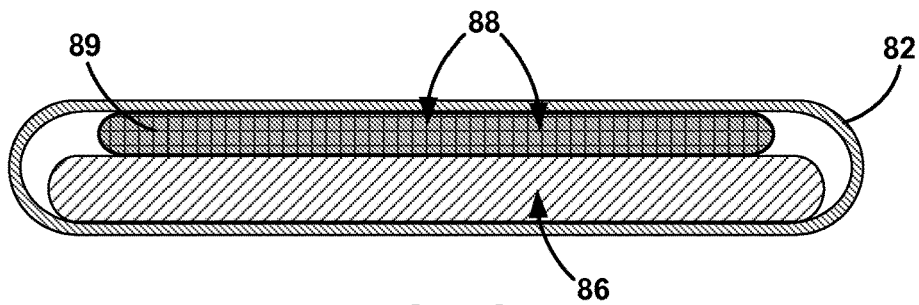

FIGS. 6A, 6B, and 6C are cross-sectional top and side views of phase change material disposed in disk-shaped volume 88 adjacent to the in-plane spiral of flexible coil 86. Energy transfer device 80 is an example of energy transfer device 26 of FIG. 1. As shown in FIG. 6A, energy transfer device 80 includes flexible coil 86, flexible housing 82, connector portion 84, and phase change material disposed in disk-shaped volume 88 (e.g., a doughnut shaped volume). FIG. 6A shows energy transfer device 80 with the top of flexible housing 82 removed to expose flexible coil 86 and disk-shaped volume 88 of phase change material adjacent flexible coil 86 in a plane parallel to the plane of flexible coil 86. Flexible coil 86 is shown as a solid component in FIGS. 6A, 6B, and 6C for ease of illustration, but flexible coil 86 may be an in-plane spiral of wire similar to that of flexible coil 28 of FIG. 2A.

Energy transfer device 80 includes phase change material disposed in disk-shaped volume 88 of a plane adjacent and parallel to the in-plane spiral of flexible coil 86. Disk-shaped volume 88 may be disposed such that the large flat surface area of disk-shaped volume 88 is positioned to contact the large flat surface area of flexible coil 86. In other words, disk-shaped volume 88 may be one layer of energy transfer device 80 and flexible coil 86 may be a second layer of the device. The increased contact area between disk-shaped volume 88 and flexible coil 86 may increase the thermal communication to the phase change material and improve the heat management of energy transfer device 80. Disk-shaped volume 88 may have a thickness and diameter slightly less than that of flexible coil 86. In other examples, disk-shaped volume 88 may have a thickness and diameter equal to or greater than flexible coil 86.

FIG. 6B is an illustration of a cross-section of energy transfer device 80 indicated by section 6B in FIG. 6A. Flexible coil 86 is shown with phase change material disposed disk-shaped volume 88 on top of and adjacent to flexible coil 86. The thickness of energy transfer device 80 may be larger than the thickness of the wire in flexible coil 86 because energy transfer device 80 includes the additional layer of the phase change material in disk-shaped volume 88. Flexible housing 82 also encases both flexible coil 86 and the phase change material of disk-shaped volume 88. Although the spaces around disk-shaped volume 88 and flexible coil 86 may be filled with air or other gas, the spaces may instead be filled with a thermally conductive fluid or deformable material.

Similar to energy transfer device 34 of FIG. 3B, energy transfer device 80 may also include a flexible tube or bladder to contain the phase change material in disk-shaped volume 88. This flexible tube may be a thermally conductive material that is also flexible. In some examples, the flexible tube or bladder may include compartments or sections that prevent movement of the phase change material in the liquid state. In other examples, flexible housing 82 may contain the phase change material in a separate compartment, e.g., disk-shaped volume 88, than that of flexible coil 86.

In alternative examples, flexible housing 82 may include one or more channels configured to contain the phase change material or a containment structure and/or a film may be used to contain the phase change material in the disk-shaped volume 88. Flexible housing 82 may then encase the containment structure for disk-shaped volume 88 of the phase change material. In another example, disk-shaped volume 88 may be filled with a plurality of individual beads that each contain phase change material.

FIG. 6C is an illustration of a cross-section of energy transfer device 80 indicated by section 6B in FIG. 6A. FIG. 6C may be similar to FIG. 6B; however, woven material 89 may be used to retain the phase change material in disk-shaped volume 88. Woven material 89 may be constructed of a natural or synthetic fiber that promotes wicking of the phase change material in the liquid state. Instead of pooling within disk-shaped volume 88 or within flexible housing 82, the liquid phase change material may adhere to woven material 89 via capillary action or other molecular forces. Therefore, the phase change material may be placed in contact with woven material 89 to retain the phase change material in thermal communication with flexible coil 86. Although woven material 89 may be only encased by flexible housing 82, woven material 89 may also be contained by a bladder, flexible tube, film, or other cavity.

Figure 7A:
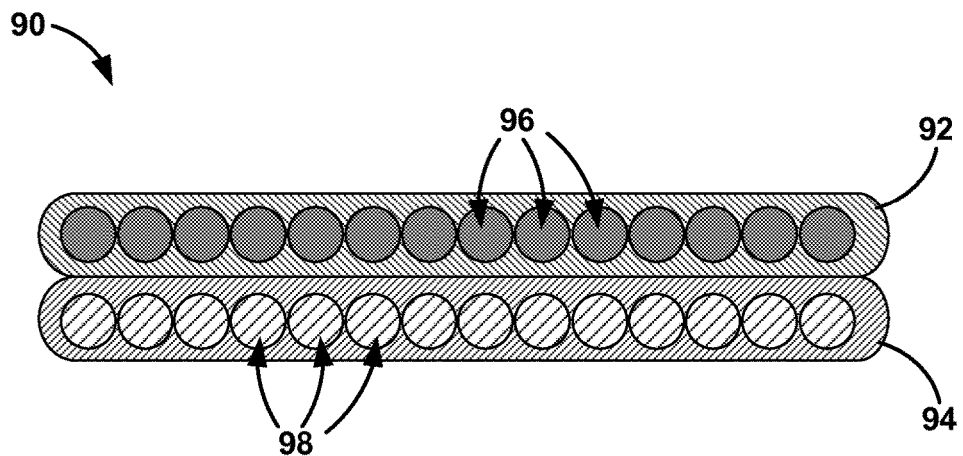
FIGS. 7A and 7B are cross-sectional side views of a phase change material disposed on one side and on an opposing side of a flexible coil.
Figure 7B:
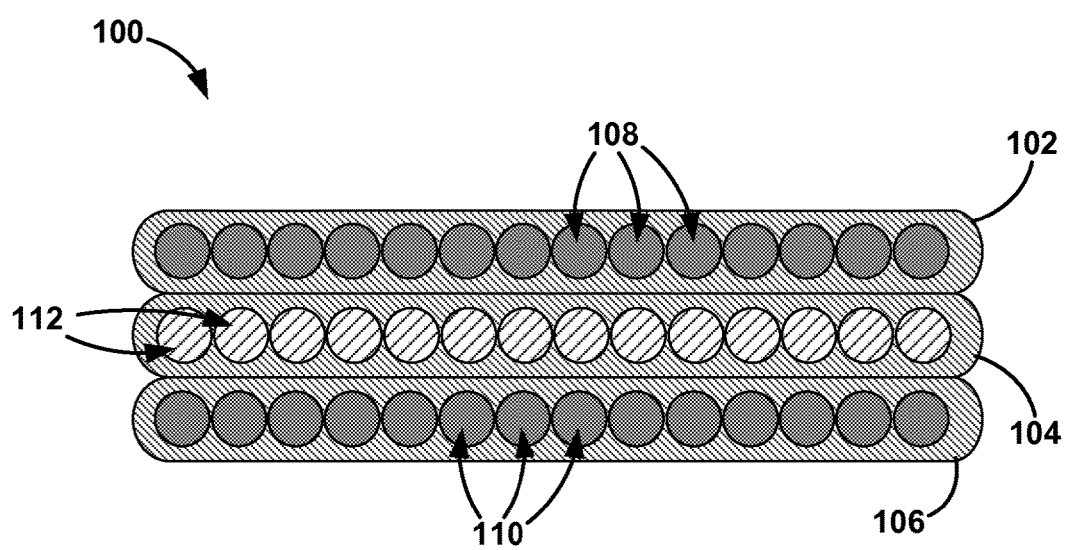

FIGS. 7A and 7B are cross-sectional side views of phase change material 96 disposed on one side and opposing sides of a flexible coil. Energy transfer devices 90 and 100 are examples of energy transfer device 26 of FIG. 1. As shown in FIG. 7A, energy transfer device 90 includes phase change material 96 in a spiral configuration on one side of flexible coil 98. In other examples, phase change material 96 may be contained within flexible tubes, channels, beads, or any other containment structure. Flexible coil 98 is also shown as an in-plane spiral of wire. Similar to other flexible coils described here, wires may be coupled to opposite ends of the in-plane spiral such that the charging circuit can drive electrical current through flexible coil 98. Phase change material 96 may be retained in flexible housing 92, and flexible coil 98 may be retained within flexible housing 94. Flexible housings 92 and 94 may be formed separately and joined together or formed at the same time. Flexible housings 92 and 94 may facilitate thermal communication between flexible coil 98 and phase change material 96.

As shown in FIG. 7B, energy transfer device 90 includes phase change material disposed on opposing sides of flexible coil 112 (e.g., a coil of multiple turns of wire). Energy transfer device 100 includes phase change material 108 in a spiral configuration on one side of flexible coil 112. In addition, phase change material 110 is included in a spiral configuration on the opposing side of flexible coil 112. Phase change material 108 and 110 may be contained within flexible tubes, channels, beads, or any other containment structure. Flexible coil 112 is also shown as an in-plane spiral of wire. Phase change materials 108 and 110 may be retained in flexible housings 102 and 106, respectively. Flexible coil 112 may be retained within flexible housing 104. Flexible housings 102, 104, and 106 may be formed separately and joined together or formed at the same time. Flexible housings 102, 104, and 106 may also facilitate thermal communication between flexible coil 112 and phase change materials 108 and 110.

In the examples of FIGS. 7A and 7B, phase change materials 96, 108, and 110 may each be contained within channels of the respective flexible housings 92, 102, and 106. These channels may not require the use of any other material to contain or retain the phase change material. However, additional containment structures, e.g., flexible tubes, may also be included within the channels. Although the channels are illustrated with a circular cross-section, the channels may be constructed of any shape. For example, the channels have square, rectangular, oval, or unsymmetrical cross-sections.

Figure 8A:
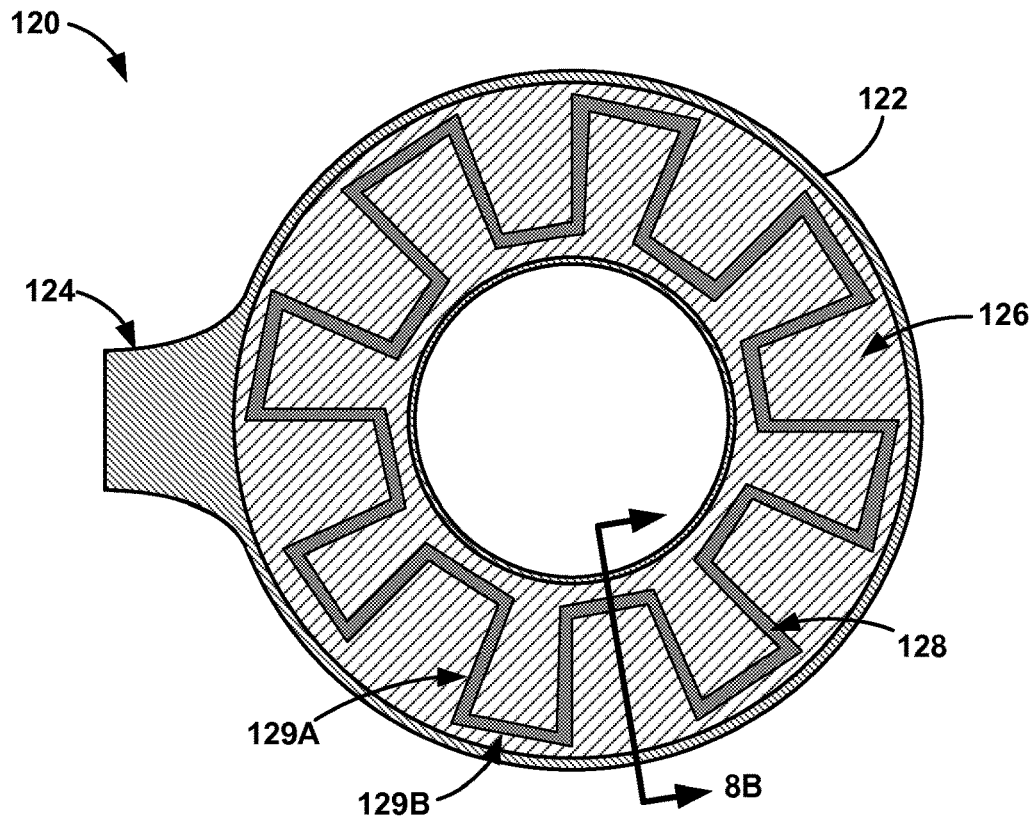
FIGS. 8A and 8B are cross-sectional side views of a phase change material disposed in a radial zigzag pattern adjacent to the in-plane spiral of a flexible coil.
Figure 8B:
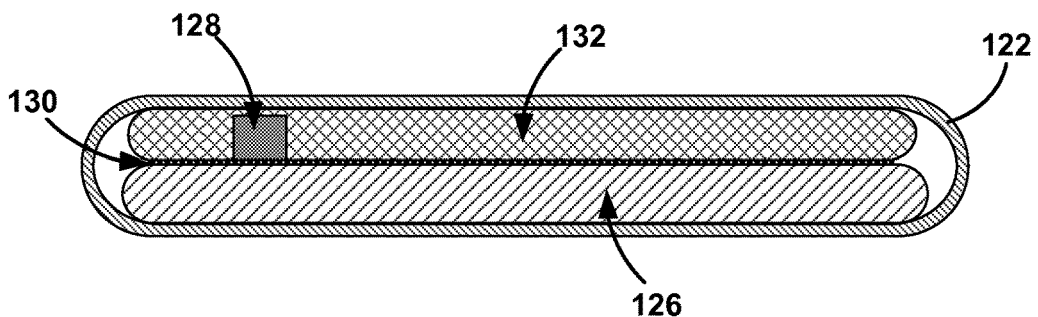

FIGS. 8A and 8B are cross-sectional side views of a phase change material disposed in radial zigzag pattern 128 adjacent to the in-plane spiral of flexible coil 126. Energy transfer device 120 is an example of energy transfer device 26 of FIG. 1. As shown in FIG. 8A, energy transfer device 120 includes flexible coil 126, phase change material in radial zigzag pattern 128, flexible housing 122, and connector portion 124. FIG. 8A shows energy transfer device 120 with the top of flexible housing 122 removed to expose flexible coil 126 and radial zigzag pattern 128 on top of, or adjacent to, flexible coil 126. Flexible coil 126 is shown as a solid component in FIGS. 8A and 8B for ease of illustration, but flexible coil 126 may be an in-plane spiral of wire similar to that of flexible coil 28 of FIG. 2A.

Energy transfer device 120 includes phase change material disposed in radial zigzag pattern 128 adjacent to the in-plane spiral of flexible coil 126. Radial zigzag pattern 128 includes radial sections 129A that extend between the inner and outer diameter of flexible coil 126 and circumferential sections 129B that extend around the circumference of flexible coil 126. This configuration of radial zigzag pattern 128 may be configured to promote curvature of flexible coil 126 and energy transfer device 120 in predetermined directions. For example, radial zigzag pattern 128 may promote flexibility or curvature of energy transfer device 120 across the circumference of energy transfer device 120. In other words, energy transfer device 120 may more easily deform at any circumferential position across the center of energy transfer device 120.

As shown in FIG. 8A, radial zigzag pattern 128 includes 16 radial segments 129A and 16 circumferential sections 129B. However, radial zigzag pattern 128 may include fewer or greater radial and circumferential sections in other example. A radial zigzag pattern 128 with more segments may increase the mass of phase change material in energy transfer device 120 that in turn provides a larger heat sink for flexible coil 126. The phase change material in radial zigzag pattern 128 may reside flat against flexible coil 126 to promote thermal communication between flexible coil 126 and the phase change material. Radial zigzag pattern 128 may be disposed on one side of flexible coil 126 or on both opposing sides of flexible coil 126 in other examples.

FIG. 8B is an illustration of a cross-section of energy transfer device 120 indicated by section 8B in FIG. 8A. Flexible coil 126 is shown with the phase change material of radial zigzag pattern 128 on top of and adjacent to flexible coil 126. The thickness of energy transfer device 120 may be greater than the thickness of the wire in flexible coil 126 because energy transfer device 120 includes a layer of phase change material. Flexible housing 122 also encases both flexible coil 126 and the phase change material of radial zigzag pattern 128.

Radial zigzag pattern 128 may be formed by channels within containment structure 132. Containment structure 132 may be constructed of a thermally conductive or thermally insulative material that is also flexible. Film 130 may be applied to the surface of containment structure 132 to retain the phase change material within the channels of containment structure 132. Film 130 may be adhered to containment structure 132 with an adhesive or other bonding technique. Film 130 may also be configured to contact flexible coil 126 and transfer heat to the phase change material in radial zigzag pattern 128. Alternatively, containment structure 132 may include two mating portions that are filled with the phase change material and, when combined, contain the phase change material in the channels of the two mating portions.

Similar to energy transfer device 34 of FIG. 3B, energy transfer device 120 may alternatively include one or more flexible tubes, beads, or a woven material to contain the phase change material in radial zigzag pattern 128 at predetermined locations with respect to flexible coil 126. In other examples, radial zigzag pattern 128 may be formed in one or more channels or cavities of flexible housing 122.

Figure 9A:
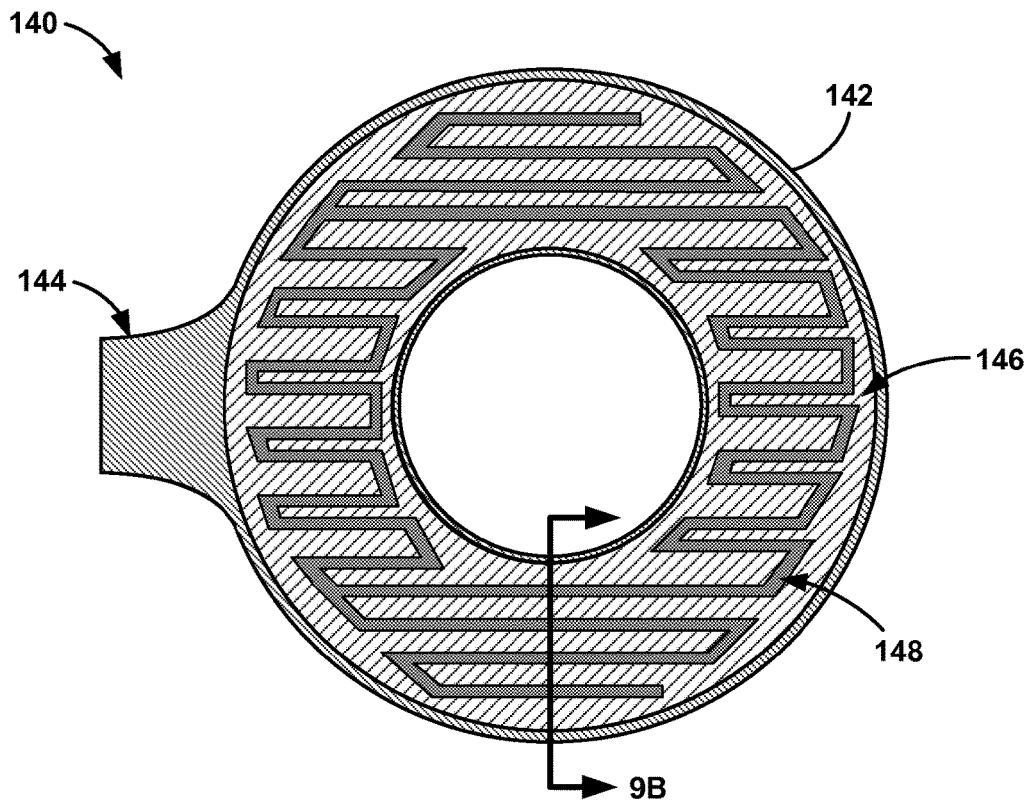
FIGS. 9A and 9B are cross-sectional side views of a phase change material disposed in a lateral zigzag pattern adjacent to the in-plane spiral of a flexible coil.
Figure 9B:
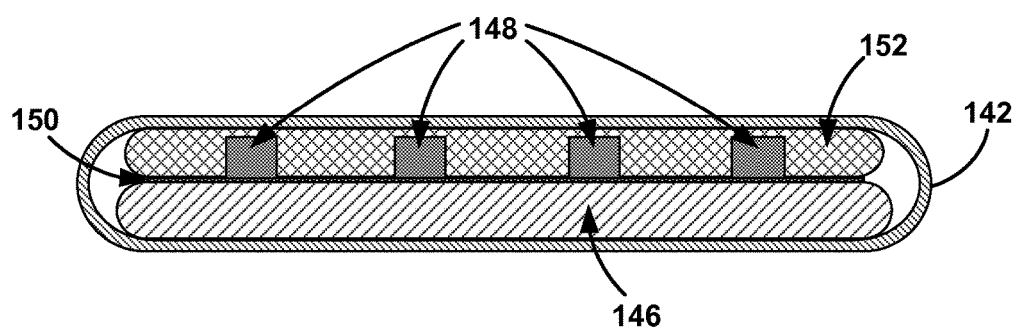

FIGS. 9A and 9B are cross-sectional side views of a phase change material disposed in lateral zigzag pattern 148 adjacent to the in-plane spiral of flexible coil 146. Energy transfer device 140 is an example of energy transfer device 26 of FIG. 1. As shown in FIG. 9A, energy transfer device 140 includes flexible coil 146, phase change material in radial zigzag pattern 148, flexible housing 142, and connector portion 144. FIG. 9A shows energy transfer device 140 with the top of flexible housing 148 removed to expose flexible coil 148 and radial zigzag pattern 148 on top of, or adjacent to, flexible coil 146. Flexible coil 146 is shown as a solid component in FIGS. 9A and 9B for ease of illustration, but flexible coil 146 may be an in-plane spiral of wire similar to that of flexible coil 28 of FIG. 2A.

Energy transfer device 140 includes phase change material disposed in lateral zigzag pattern 148 adjacent to the in-plane spiral of flexible coil 146. Lateral zigzag pattern 148 may be similar to radial zigzag pattern 128 of FIG. 8A, but lateral zigzag pattern 148 traverses the surface of flexible coil 146 from one side edge of energy transfer device 140 to the other side. This configuration of lateral zigzag pattern 148 may be configured to promote curvature of flexible coil 146 and energy transfer device 140 in predetermined directions. For example, lateral zigzag pattern 148 may promote flexibility or curvature of energy transfer device 140 in a single direction across the energy transfer device 140. In other words, lateral zigzag pattern 148 may promote curling of energy transfer device 140 from the endpoints of lateral zigzag pattern 148 toward the middle of energy transfer device 140. In other examples, lateral zigzag pattern 148 may be oriented in any direction across flexible coil 146. Lateral zigzag pattern 148 may include any number of sections to cover less or more area of flexible coil 146 with phase change material. Lateral zigzag pattern 148 may be disposed on one side of flexible coil 146 or on both opposing sides of flexible coil 146 in other examples.

FIG. 9B is an illustration of a cross-section of energy transfer device 140 indicated by section 9B in FIG. 9A. Flexible coil 146 is shown with the phase change material of lateral zigzag pattern 148 on top of and adjacent to flexible coil 146. The thickness of energy transfer device 140 may be greater than the thickness of the wire in flexible coil 146 because energy transfer device 140 includes a layer of phase change material. Flexible housing 142 also encases both flexible coil 146 and the phase change material of lateral zigzag pattern 148.

Similar to radial zigzag pattern 128 of FIG. 8B, lateral zigzag pattern 148 may be formed by channels within containment structure 132. Film 150 may be provided to seal the phase change material within the channels of containment structure 152. Containment structure 152 may be constructed of a thermally conductive or thermally insulative material that is also flexible. Film 150 may be applied to the surface of containment structure 152 to retain the phase change material within the channels of containment structure 152. Film 130 may be adhered to containment structure 152 with an adhesive or other bonding technique. Film 150 may also be configured to contact flexible coil 146 and transfer heat to the phase change material in lateral zigzag pattern 148. Alternatively, containment structure 152 may include two mating portions that are filled with the phase change material and, when combined, contain the phase change material in the channels of the two mating portions.

Similar to energy transfer device 34 of FIG. 3B, energy transfer device 140 may alternatively include one or more flexible tubes, beads, or a woven material to contain the phase change material in lateral zigzag pattern 148 at predetermined locations with respect to flexible coil 146. In other examples, lateral zigzag pattern 148 may be formed in one or more channels or cavities of flexible housing 122.

Figure 10A:
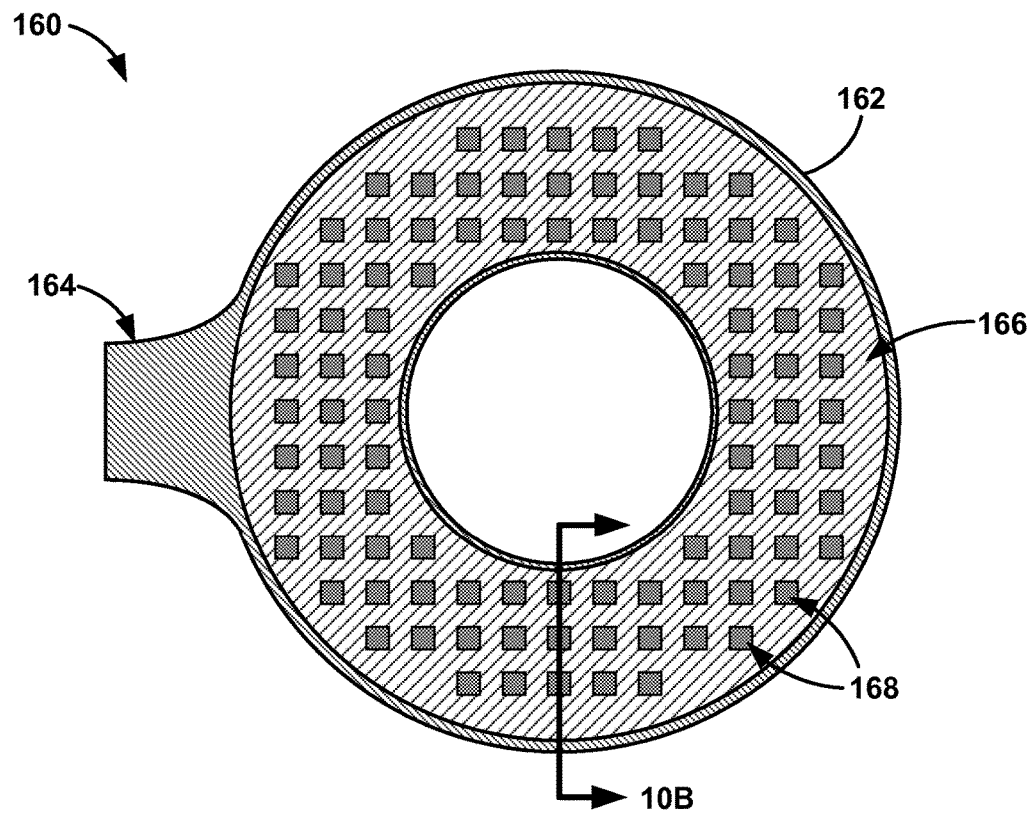
FIGS. 10A and 10B are cross-sectional side views of a phase change material disposed in a plurality of self-contained volumes distributed adjacent a flexible coil.
Figure 10B:
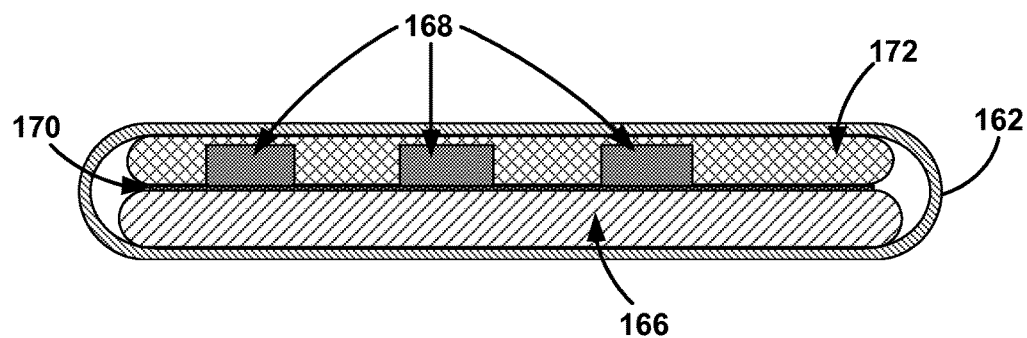

FIGS. 10A and 10B are cross-sectional side views of phase change material disposed in a plurality of self-contained volumes 168 distributed adjacent flexible coil 166. Energy transfer device 160 is an example of energy transfer device 26 of FIG. In addition, energy transfer device 160 may be very similar to energy transfer device 140 of FIGS. 9A and 9B. However, energy transfer device 160 may include a plurality of self-contained volumes 168 instead of a continuous zigzag pattern. Energy transfer device 160 includes flexible coil 166, phase change material in self-contained volumes 168, flexible housing 162, and connector portion 164. The phase change material of self-contained volumes 168 may be provided on one or both sides of flexible coil 166. Volumes 168 may, in effect, form multiple, discrete islands of phase change material distributed across the area of energy transfer device 160.

Self-contained volumes 168 may be any depression, cavity, or encapsulated volume that contains phase change material. For example, self-contained volumes 168 may be a plurality of individual beads or capsules. Each of the beads or capsules may include phase change material encapsulated with a thermally conductive material, such as an inert and chemically stable polymer. Many small volumes of phase change material may prevent phase change material from pooling or migrating when the phase change material is heated to the liquid state. Many self-contained volumes 168 may also promote flexibility of energy transfer device 160. Energy transfer device 160 may include any number of self-contained volumes 168. In general, energy transfer device 160 may include as few as 2 self-contained volumes or more than one hundred self-contained volumes. Self-contained volumes 168 may be distributed in a grid, concentric circles, a random pattern, or any other pattern selected to perform the functions described herein.

FIG. 10B is an illustration of a cross-section of energy transfer device 160 indicated by section 10B in FIG. 10A. Flexible coil 166 is shown with the phase change material of self-contained volumes 168 on top of and adjacent to flexible coil 166. The thickness of energy transfer device 140 may be greater than the thickness of the wire in flexible coil 166 because energy transfer device 160 includes a layer of phase change material. Flexible housing 162 also encases both flexible coil 166 and the phase change material of self-contained volumes 168.

Self-contained volumes 168 may be formed as cavities or depressions within containment structure 132. Film 170 may be provided to seal the phase change material within the cavities of containment structure 172. Containment structure 172 may be constructed of a thermally conductive or thermally insulative material that is also flexible. Film 170 may be applied to the surface of containment structure 172 to retain the phase change material within the cavities of containment structure 172. Film 150 may be adhered to containment structure 152 with an adhesive or other bonding technique. Film 170 may also be configured to contact flexible coil 166 and transfer heat to the phase change material in self-contained volumes 168. Alternatively, containment structure 152 may include two mating portions that are filled with the phase change material and, when combined, contain the phase change material in the channels of the two mating portions. Self-contained volumes 168 may be shaped as spheres, cubes, domes, or any other shapes.

Similar to energy transfer device 34 of FIG. 3B, energy transfer device 160 may alternatively include one or more flexible tubes, beads, or a woven material to contain the phase change material in self-contained volumes 168 at predetermined locations with respect to flexible coil 166. In other examples, self-contained volumes 168 may be formed in one or more cavities or depressions of flexible housing 122. Alternatively, self-contained volumes 168 may each be a bead or other encapsulation structure that retains the phase change material.

According to the techniques and devices described herein, phase change material may be provided within an energy transfer device to manage the temperature of a flexible coil. The phase change material may be disposed in relation to the flexible coil such that heat is conducted to the phase change material. In addition, the phase change material may be configured to be positioned between the skin of a patient and the flexible coil, on the opposite side of the flexible coil than the skin, or some combination thereof. Further, the phase change material may be retained within predetermined locations with respect to the flexible coil such that the phase change material does not interfere with or otherwise reduce the flexibility of the flexible coil. This disclosure also describes a method that includes transmitting energy from a flexible primary coil associated with an external recharge device to a secondary coil of an implantable medical device and absorbing heat from the flexible primary coil via a phase change material configured to deform with the flexible coil.

Although the phase change material in energy transfer devices is generally described has contained or separated from the wire of the flexible coil, the phase change material may come in contact with the flexible coil. In other words, the phase change material may be disposed within the flexible housing and allowed to flow along and within the flexible coil when in the liquid state. Therefore, the energy transfer device may not require a tube or other containment mechanism for separating the phase change material from the flexible coil while maintaining thermal communication between the phase change material and the flexible coil.

Various examples have been described. These and other examples are within the scope of the following claims.

What is claimed is:

1. A device comprising:
   a flexible coil configured to at least one of transmit electrical energy to or receive electrical energy from a second coil via inductive coupling; and
   a phase change material configured in one or more shapes that allow the phase change material in a solid state to deform with the flexible coil, wherein the phase change material is configured to absorb heat from the flexible coil.

2. The device of claim 1, further comprising a flexible housing configured to encase the flexible coil and the phase change material.

3. The device of claim 2, wherein the flexible coil is configured to conform to a non-planar skin surface, and wherein the flexible housing is configured to deform with the flexible coil.

4. The device of claim 2, wherein the flexible housing comprises one or more channels configured to contain the phase change material in the one or more shapes.

5. The device of claim 1, further comprising:
   a containment structure comprising one or more channels configured to contain the phase change material in the one or more shapes; and
   a film configured to be applied to a surface of the containment structure, retain the phase change material within the one or more channels, and contact the flexible coil.

6. The device of claim 1, further comprising one or more flexible tubes configured to contain the phase change material in the one or more shapes at predetermined locations with respect to the flexible coil, wherein the phase change material is disposed within the one or more flexible tubes.

7. The device of claim 6, wherein the one or more flexible tubes are constructed of a thermally conductive elastomer.

8. The device of claim 1, further comprising a woven material, wherein the phase change material is placed in contact with the woven material to retain the phase change material in thermal communication with the flexible coil.

9. The device of claim 1, wherein the phase change material is encapsulated in a plurality of beads distributed adjacent at least one surface of the flexible coil, the plurality of beads comprising the one or more shapes.

10. The device of claim 1, wherein the flexible coil comprises a wire wound as an in-plane spiral.

11. The device of claim 10, wherein the phase change material is disposed in a disk-shaped volume of a second plane adjacent to the in-plane spiral.

12. The device of claim 10, wherein the phase change material is disposed within the in-plane spiral as at least one phase change material spiral, the at least one phase change material spiral comprising at least one shape of the one or more shapes.

13. The device of claim 10, wherein the phase change material is disposed in a plurality of concentric rings in a second plane adjacent to the in-plane spiral, the plurality of concentric rings comprising at least some of the one or more shapes.

14. The device of claim 10, wherein the phase change material is disposed at least one of inside an inner diameter of the in-plane spiral or outside an outer diameter of the in-plane spiral.

15. The device of claim 10, wherein the phase change material is disposed in a zigzag pattern adjacent to the in-plane spiral and configured to promote curvature of the flexible coil in predetermined directions, the zigzag pattern comprising at least one of the one or more shapes.

16. The device of claim 1, wherein the phase change material is disposed on opposing sides of the flexible coil.

17. The device of claim 1, wherein the phase change material comprises a melting point temperature between approximately 35 degrees Celsius and 43 degrees Celsius.

18. The device of claim 1, wherein the flexible coil is coupled to a charging device configured to transcutaneously charge a rechargeable power source of an implantable medical device via inductive coupling between the flexible coil and the second coil, and wherein the implantable medical device comprises the second coil.

19. A device comprising:
a flexible coil configured to at least one of transmit electrical energy to or receive electrical energy from a second coil via inductive coupling; and
means for absorbing heat from the flexible coil, wherein the means for absorbing heat is configured in one or more shapes that allows the means for absorbing heat in a solid state to deform with the flexible coil.

20. The device of claim 19, further comprising means for encasing the flexible coil and the means for absorbing the heat from the flexible coil.

21. The device of claim 20, wherein the flexible coil is configured to conform to a non-planar skin surface, and wherein the means for encasing the flexible coil is configured to deform with the flexible coil.

22. The device of claim 20, further comprising means for containing the means for absorbing heat in the one or more shapes at predetermined locations with respect to the flexible coil.

23. The device of claim 19, wherein the containing means comprises one or more channels as the one or more shapes.

24. The device of claim 19, wherein the containing means comprises one or more flexible tubes that contain the means for absorbing heat in the one or more shapes, wherein the phase change material is disposed within the one or more flexible tubes.

25. The device of claim 19, further comprising means for encapsulating the means for absorbing heat at a plurality of isolated locations distributed adjacent to at least one surface of the flexible coil, the means for encapsulating the means for absorbing heat comprising the one or more shapes.

26. The device of claim 19, wherein the flexible coil comprises a wire wound as an in-plane spiral.

27. The device of claim 19, wherein the means for absorbing heat is disposed on opposing sides of the flexible coil.

28. The device of claim 19, wherein the means for absorbing heat comprises a melting point temperature between approximately 35 degrees Celsius and 43 degrees Celsius.

29. A system comprising:
an implantable medical device comprising a first coil;
a flexible coil configured to transmit electrical energy to the first coil of the implantable medical device via inductive coupling, wherein the flexible coil is configured to conform to a non-planar exterior skin surface;
a phase change material disposed in one or more shapes selected to allow the phase change material in a solid state to deform with the flexible coil when the phase change material is disposed at one or more positions adjacent to the flexible coil, wherein the phase change material is configured to absorb heat from the flexible coil; and
a flexible housing configured to encase the flexible coil and the phase change material.

30. The system of claim 29, wherein the flexible housing comprises one or more channels configured to contain the phase change material in the one or more shapes.

31. The system of claim 29, further comprising:
a containment structure comprising one or more channels configured to contain the phase change material in the one or more shapes; and
a film configured to be applied to a surface of the containment structure, retain the phase change material within the one or more channels, and contact the flexible coil.

32. The system of claim 29, further comprising one or more flexible tubes configured to contain the phase change material in the one or more shapes at the one or more positions, wherein the phase change material is disposed within the one or more flexible tubes.

33. The system of claim 29, wherein the phase change material is disposed on opposing sides of the flexible coil.

34. A method comprising:
transmitting electrical energy from a flexible primary coil associated with an external recharge device to a secondary coil of an implantable medical device; and
absorbing heat from the flexible primary coil via a phase change material configured in one or more shapes that allow the phase change material in a solid state to deform with the flexible primary coil.

35. A system comprising:
an implantable medical device comprising a first coil and a rechargeable power source; and
an external charging device comprising:
- a flexible coil configured to transmit electrical energy to the first coil of the implantable medical device via inductive coupling; and
- a phase change material configured in one or more shapes that allow the phase change material in a solid state to deform with the flexible coil, wherein the phase change material is configured to absorb heat from the flexible coil, wherein the external charging device is configured to transcutaneously charge the rechargeable power source of the implantable medical device via inductive coupling between the flexible coil and the first coil.

* * * * *